United States Patent
Blanchard

(10) Patent No.: US 11,724,254 B2
(45) Date of Patent: Aug. 15, 2023

(54) LIQUID TRANSFER SYSTEM

(71) Applicant: Thrive Bioscience, Inc., Beverly, MA (US)

(72) Inventor: Alan Blanchard, Topsfield, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 348 days.

(21) Appl. No.: 16/614,487

(22) PCT Filed: May 18, 2018

(86) PCT No.: PCT/US2018/033350
§ 371 (c)(1),
(2) Date: Nov. 18, 2019

(87) PCT Pub. No.: WO2018/213682
PCT Pub. Date: Nov. 22, 2018

(65) Prior Publication Data
US 2020/0070144 A1    Mar. 5, 2020

Related U.S. Application Data

(60) Provisional application No. 62/508,883, filed on May 19, 2017.

(51) Int. Cl.
*B01L 3/02* (2006.01)
*C12M 1/34* (2006.01)
(Continued)

(52) U.S. Cl.
CPC .......... *B01L 3/0275* (2013.01); *C12M 33/04* (2013.01); *C12M 41/14* (2013.01); *C12M 41/40* (2013.01);
(Continued)

(58) Field of Classification Search
None
See application file for complete search history.

(56) References Cited

U.S. PATENT DOCUMENTS

| 4,877,585 A | 10/1989 | Perlman |
| 5,779,984 A * | 7/1998 | Kelly .................. B65D 25/108 |
| | | 206/486 |

(Continued)

FOREIGN PATENT DOCUMENTS

| CH | 708562 A2 | 3/2015 |
| CN | 86200931 U | 11/1986 |

(Continued)

OTHER PUBLICATIONS

PCT/US2018/033350, Sep. 28, 2018, International Search Report and Written Opinion.

(Continued)

*Primary Examiner* — Matthew D Krcha
*Assistant Examiner* — Brittany I Fisher
(74) *Attorney, Agent, or Firm* — Wolf, Greenfield & Sacks, P.C.

(57) ABSTRACT

Aspects of the invention relate to liquid transfer systems including a pipette tip having a body defining an inner volume and having first and second ends, the first end arranged to transfer a volume of liquid into and out of the pipette tip and the second end arranged for attachment to a pipette, and a bladder sealingly attached to the body. In some embodiments, the bladder is disposable in the inner volume. The bladder may be defined by a membranous sac and/or a planar membrane. The bladder may be moveable in response to an applied pressure to transfer liquid. The bladder also may be stretchable to accommodate a volume of fluid. In some embodiments, the pipette tip is used in a cell culture (Continued)

incubator, with a manipulator including a pipette that is in fluid communication with the pipette tip.

22 Claims, 12 Drawing Sheets

(51) Int. Cl.
*B01L 9/00* (2006.01)
*C12M 1/26* (2006.01)
*C12M 1/00* (2006.01)

(52) U.S. Cl.
CPC . *B01L 2200/0689* (2013.01); *B01L 2300/123* (2013.01); *B01L 2400/0481* (2013.01)

(56) References Cited

U.S. PATENT DOCUMENTS

| | | | |
|---|---|---|---|
| 6,117,394 A | 9/2000 | Smith | |
| 6,475,440 B1 | 11/2002 | Bochkariov | |
| 6,499,362 B1 | 12/2002 | Wolcott | |
| 6,874,379 B2 | 4/2005 | Matsuda et al. | |
| 7,318,911 B2 | 1/2008 | Smith | |
| 2002/0009809 A1 | 1/2002 | Brewer | |
| 2004/0214200 A1 | 10/2004 | Brown et al. | |
| 2013/0283884 A1* | 10/2013 | Beroz | B01L 3/0275 73/1.74 |
| 2017/0008687 A1* | 1/2017 | Koptis | B65D 81/325 |
| 2017/0326542 A1* | 11/2017 | Beroz | B01L 3/0217 |

FOREIGN PATENT DOCUMENTS

| | | |
|---|---|---|
| CN | 1447718 A | 10/2003 |
| CN | 2868404 Y | 2/2007 |
| CN | 101249463 A | 8/2008 |
| CN | 101375169 A | 2/2009 |
| CN | 102740978 A | 10/2012 |
| CN | 204564168 U | 8/2015 |
| CN | 105181979 A | 12/2015 |
| CN | 105498877 A | 4/2016 |
| CN | 106311369 A | 1/2017 |
| DE | 102006046542 | 4/2008 |
| EP | 0264704 A2 | 4/1988 |
| FR | 2225211 A1 | 11/1974 |
| GB | 1471592 A | 4/1977 |
| JP | H04-45856 A | 2/1992 |
| JP | H08-219956 A | 8/1996 |
| JP | 2000-140655 A | 5/2000 |
| JP | 2010-156545 A | 7/2010 |
| WO | WO 98/00718 A1 | 1/1998 |
| WO | WO 2015/036355 A1 | 3/2015 |
| WO | WO 2016/161163 A2 | 10/2016 |

OTHER PUBLICATIONS

PCT/US2018/033350, Nov. 28, 2019, International Preliminary Report on Patentability.
International Search Report and Written Opinion dated Sep. 28, 2018 in connection with Application No. PCT/US2018/033350.
International Preliminary Report on Patentability dated Nov. 28, 2019 in connection with Application No. PCT/US2018/033350.

* cited by examiner

LIQUID TRANSFER SYSTEM

CROSS REFERENCE TO RELATED APPLICATIONS

This application is a national stage filing under 35 U.S.C. 371 of International Application No. PCT/US2018/033350, filed on May 18, 2018, which claims the benefit under 35 U.S.C. §119; (e) to U.S. Provisional Application Ser. No. 62/508,883, entitled "LIQUID TRANSFER SYSTEM" and filed on May 19, 2017. The entirety of each of the applications listed above is herein incorporated by reference.

FIELD

Aspects relate to a liquid transfer system and methods for using the system to transfer a volume of liquid into and out of a pipette tip. Some aspects relate to using such a liquid transfer system in cell culture incubators and to methods for using such incubators.

BACKGROUND

Pipettes are used to transfer a volume of liquid, such as transferring media containing cells between cell culture vessels. Cell culture is a useful technique in both research and clinical contexts. For example, culture of mammalian cells is often performed in order to establish clonal cell lines, tissue preparations, in vitro fertilization preparations, or to expand populations of stem cells.

SUMMARY

Presently available pipette tips may introduce contaminants into a sample in the pipette tip. For example, because the pipette tip is open at an end adjacent a pipette, which is used to transfer many different samples into and out of numerous pipette tips, cross-contamination may occur. In embodiments using such pipette tips in a cell cultures, this may lower culture efficiency and repeatability. Additionally, because traditional pipette tips are designed for a single use only, a large volume of waste (e.g., a large pile of used tips) may result during an experiment such as a cell culture being performed in an incubator. Single-use pipette tips also may need a large area for storage. As such, according to some aspects, the instant document provides a liquid transfer system having a pipette tip arranged to minimize or even eliminate cross contamination and to also reduce waste and/or storage space.

According to one aspect, the instant document provides a pipette tip with a body defining an inner volume and having first and second ends, the first end arranged to pass a liquid into and out of the pipette tip and the second end arranged for attachment to a pipette, and a bladder sealingly attached to the body. In some embodiments, the bladder is disposable in the inner volume of the body. In some embodiments, a first side of the bladder is exposed to a volume of accommodated liquid. In such embodiments, a second, opposite side may be exposed to a pipette. In some embodiments, the bladder may be attached to the second end of the body. The bladder also may be attached to the first end or at a location between the first and second ends.

In some embodiments, the bladder is arranged to accommodate a volume of liquid or a volume of air above the liquid in the pipette tip (e.g., the air used to displace a volume of liquid). According to some embodiments, the bladder is manipulated (e.g., moved, retracted, expanded, contracted, and/or stretched) to transfer a volume of liquid into or out of the pipette tip. For example, a pressure may be applied to the bladder to manipulate the bladder. In some embodiments, the bladder is arranged to move back and forth in response to an applied pressure. For example, the bladder may be at least partially retracted outside of the pipette tip body to draw a volume of liquid into the pipette tip in response to a negative pressure. In response to a positive pressure, the bladder may be retracted into the pipette tip (e.g., into the inner volume of the pipette tip body) to expel at least a portion of the volume of liquid from the pipette tip. In other embodiments, the bladder is configured to expand and contract in response to the applied pressure. The bladder also may be arranged stretch in response to the applied pressure.

In some embodiments, the negative pressure creates a vacuum that is applied to the bladder. For example, a negative pressure differential may be created between the air pressure in a container (e.g., the air pressure in the tip) and the air pressure of the environment. In such embodiments, the pressure differential or pressure gradient may be applied across the bladder.

According to one aspect, the bladder includes a membranous sac that is arranged to accommodate the volume of liquid. In some embodiments, the bladder is disposable in the body of the pipette tip, with the formed, membranous sac folded into the tip. For example, the bladder may be disposed in the pipette tip such that the membranous sac extends from a location at the second end, or between the first and second ends, toward the first end.

In other embodiments, the bladder includes a planar membrane. In some embodiments, the planar membrane may include an unformed state of a membranous sac. For example, an elastomeric membrane may be disposed in the tip, with the membrane having a planar configuration in a resting state. Once a pressure (e.g., a negative pressure) is applied to the membrane, the membrane may be stretched and/or expanded such that the membrane forms the membranous sac, which may accommodate the volume of liquid. In other embodiments, the planar membrane may simple move back and forth in response to the applied pressure, without expanding and contracting. As will be appreciated, depending upon the material used create the planar membrane, a least a part of the membrane (e.g., a central portion of the membrane) may fall below the plane extending through the membrane (e.g., slightly towards the first end of the pipette tip) in response to gravity, forming a concave arrangement.

In some embodiments, the pipette tip is arranged to accommodate a volume liquid that is less than or equal to a sum of a volume of the bladder and a volume of an inner volume of the body of the pipette tip. As will be appreciated, the volume of accommodated liquid may be limited by the volume of the bladder.

In some embodiments, the volume of the bladder includes a volume defined by the membranous sac. In some embodiments, the bladder is formed of a material that allows the bladder to expand beyond the volume of the membranous sac. In such embodiments, the volume of the bladder also may include the volume of the expanded bladder (e.g., the bladder after an applied pressure greater than that needed to simply draw a liquid into the bladder).

In some embodiments, the bladder is permanently attached to the pipette tip body (e.g., to the second end of the body). In other embodiments, the bladder may be removably attached to the pipette tip body.

In some embodiments, the second end of the pipette tip is adjacent a pipette. In some embodiments, the bladder (e.g., the formed membranous sac or planar membrane) is positioned at the second end. In some embodiments, the membranous sac extends from the second end of the body towards the first end of the body.

In some embodiments, the pipette tip is reusable. The pipette tip also may be disposable such that the tip is only used for a single liquid transfer. In these situations, the pipette tip may be removably attached to the pipette.

According to yet another aspect, this document provides a liquid transfer system that includes a pipette tip having a body defining an inner volume and having first and second ends, the first end arranged to pass a liquid into and out of the pipette tip and the second end arranged for attachment to a pipette, and a bladder sealingly attached to the body. In some embodiments, the bladder is disposable in the inner volume. The system also may include a pipette attached to the pipette tip, the pipette arranged to generate pressure gradients across to the bladder to transfer a volume of liquid into and out of the pipette tip.

In some embodiments, the volume of liquid drawn into (or expelled from) the pipette tip is dependent on the first applied pressure. For example, the volume of liquid drawn into (or dispensed out of) the pipette tip may be based upon the amplitude of the pressure differential (e.g., between air in the container and the environment) and the duration of the applied pressure. As will be appreciated, the volume of liquid accommodated by the pipette tip is limited by the total volume of the pipette tip body and the volume of the bladder.

In some embodiments, the bladder may be retracted (e.g., partially retracted), expanded or stretched into the body of the pipette in response to the applied pressure. In such an embodiment, the volume of the pipette body may be greater than or equal to the volume of membrane (e.g., the volume of the bladder and/or diaphragm).

In some embodiments, the pipette body includes a pump which applies the pressure (e.g., via a fluid such as a liquid or air) to the pipette tip. In other embodiments, the pipette is connected to a fluid conduit which applies the pressure (e.g., the negative pressure) to the pipette tip via a valve and pump. As will be appreciated, the fluid conduit may be connected to a fluid supply (e.g., an air or liquid supply).

In some embodiments, the pipette includes a pipette shell disposed inside the pipette body to separate the pipette body from the pipette tip. As will be appreciated, in such embodiments, the pipette shell may further minimize cross contamination between the pipette and the liquid being drawn into the pipette tip. In some embodiments, the pipette shell is disposable. In other embodiments, the pipette shell may be reusable.

According to still another aspect, this document provides a pipette tip including a body defining an inner volume and having first and second ends, the first end arranged to pass a liquid into and out of the pipette tip and the second end arranged for attachment to a pipette, and a bladder sealingly attached to the body. In some embodiments, the bladder is disposable in the inner volume of the body. The bladder and at least a portion of the inner volume are arranged to accommodate a volume of fluid.

In some embodiments, the volume of liquid is less than or equal to a sum of the volume of the bladder and a volume of the body. In some embodiments, the bladder divides the body into first and second compartments. The first compartment may be in fluid communication with the first end and the second compartment may be in fluid communication with the second end. The second compartment may be arranged to receive at last one of a first applied pressure to draw a volume of liquid into the body and a second applied pressure to expel the volume of liquid from the pipette tip.

In some embodiments, the bladder includes a membrane (e.g., an elastomeric membrane) that has been stretched in response to an applied pressure to form a sac for accommodating a volume of liquid.

According to another aspect, this document provides a liquid transfer system including a pipette tip having a body defining an inner volume and having first and second ends, the first end arranged to pass a liquid into and out of the pipette tip and the second end arranged for attachment to a pipette, and a bladder sealingly attached to the body. In some embodiments, the bladder is disposable in the inner volume of the body. The system also includes a manipulator arranged to generate pressure gradients across the bladder to transfer a first volume of liquid into or out of the pipette tip.

In some embodiments, in response to the applied pressure, the bladder is at least partially retracted into an interior volume of the manipulator. In such embodiments, the pressure is a negative pressure and the bladder retracts to draw a volume of the liquid into the body of the pipette. In some embodiments, the manipulator is arranged to apply a pressure of air to the bladder to transfer a portion of the volume of liquid out of the pipette tip. In such embodiments, the bladder is moved into the body.

The pipette tip may be removably attachable to the manipulator. The manipulator may include a multi-tipped pipette. The pipette shell may be attached to the manipulator prior to attaching the pipette tip.

In some embodiments, the system includes a second pipette tip defining an inner volume and having a second body with third and fourth ends, the third end arranged to transfer fluid in and out of the body and the fourth end arranged for attachment to a manipulator, and a second bladder sealiningly attached to the inner volume of the second body. In some embodiments, the bladder is disposable in the second body. In such an embodiment, the manipulator also may be arranged to apply a pressure to the second bladder to transfer a second volume of liquid into or out of the third end of the pipette tip.

In some embodiments, the first and second pipette tips are configured to transfer first and second volumes, respectively, from the same cell culture vessel. In other embodiments, the first and second pipette tips transfer first and second volumes from first and second cell culture vessels, respectively.

In some embodiments, a system includes more than two pipettes (e.g., 3, 4, 5, 6, 7, 8, 9, 10, or more) having pipette tips as described in this document.

According to another aspect, this document provides a cell incubator having an internal chamber for incubation of cells in one or more cell culture vessels, a door opening from an external environment to said internal chamber, an imager arranged to imaging the cells within the internal chamber, a manipulator for manipulating the cells in the one or more cell culture vessels within the internal chamber, wherein the manipulator comprises at least one pipette configured to transfer a first volume of media comprising the cells into or out of the one or more cell culture vessels within the internal chamber, a pipette tip in fluid communication with the pipette, the pipette tip having a body defining an inner volume and having first and second ends, the first end arranged to transfer a volume of liquid into and out of the pipette tip and the second end arranged for attachment to a manipulator, and a bladder sealingly attached to the pipette tip, and a cell culture vessel transfer device for moving the one or more cell culture vessels between locations within the internal chamber. The manipulator applies a pressure to the bladder to transfer a first volume of media comprising the cells into or out of the pipette tip. In some embodiments, the first volume of media is proportional to the applied pressure. In some embodiments, the bladder is disposable within the inner volume of the pipette tip.

In some embodiments, the pipette applies a pressure to the bladder of the pipette tip to draw the first volume of media into the pipette tip. In some embodiments, the applied pressure is a negative pressure that applies a vacuum to the bladder.

In some embodiments, the incubator includes a second pipette for transferring a second volume of media containing cells into or out of one or more cell culture vessels within the internal chamber. A second pipette tip may be used with the second pipette. The second tip may have a body defining an inner volume and having third and fourth ends, the third end arranged to transfer liquid into and out of the pipette tip and the fourth end arranged for attachment to a manipulator, such as a pipette. In some embodiments, the second bladder is disposable in the inner volume of the second body. In some embodiments, the bladder includes a membranous sac extending from the fourth end, or a location between the third and fourth ends, toward the third end. In some embodiments, the fourth end is attached to the manipulator. In some embodiments, an incubator includes more than two pipettes (e.g., 3, 4, 5, 6, 7 8, 9, 10 or more), each of which can be used with a pipette tip as described in this document.

In such embodiments, the first and second pipette tips may be configured to transfer first and second volumes, respectively, out of the same cell culture vessel. In other embodiments, the first and second tips are configured to transfer first and second volumes out of first and second cell culture vessels, respectively.

According to another aspect, this document provides a pipette tip that may be nestable with other pipette tips. In some embodiments, the nested pipette tips may be compactly stored in a cartridge. In some embodiments, the pipette tips may be loaded directly onto the pipette via the cartridge.

According to still another aspect, this document provides a cartridge for dispensing pipette tips. In some embodiments, the cartridge includes a housing and two or more pipette tips. Each pipette tip includes a body defining an inner volume and having first and second ends, the first end arranged to pass a liquid into and out of the pipette tip and the second end arranged for attachment to a pipette, and a bladder sealingly attached to the body. The two or more pipette tips are nestable. In some embodiments, the bladder is disposable within the inner volume.

According to another aspect, this document provides a method of transferring a volume of liquid into or out of a pipette tip having a body defining an inner volume and having first and second ends, the first end arranged to pass a liquid into and out of the pipette tip and a second end arranged for attachment to a pipette, and a bladder sealingly attached to the body. The method includes applying a first pressure gradient across the bladder of the pipette tip to cause a volume of liquid to be drawn into the pipette tip via the first end of the body.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 2:
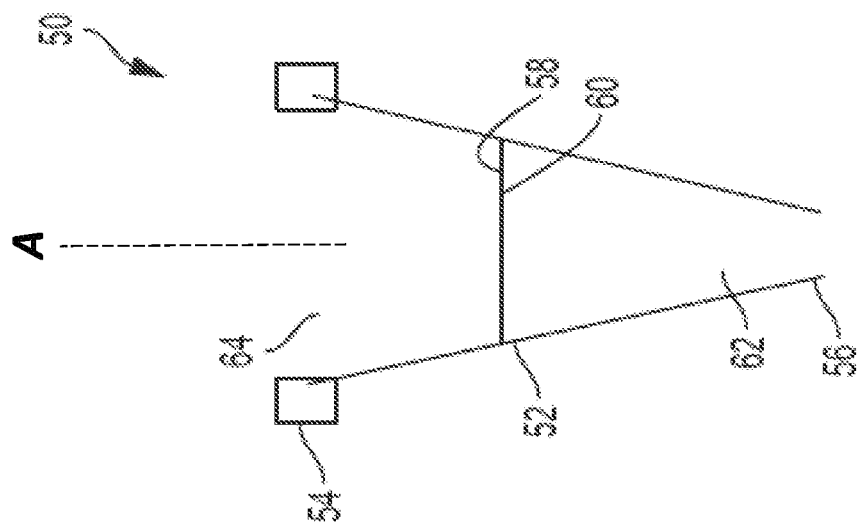
FIGS. 1 and 2 are schematic cross-sectional side views of pipette tips according to some embodiments.

Presently available pipettes are used to measure and transfer a volume liquid. For example, a pipette may draw a sample of a media containing cells from a first culture vessel and thereafter dispense the sample into a second culture vessel. Pipettes may be hand-held, with a user grasping and manipulating the pipette to transfer the measured volume of liquid. For example, with piston-driven pipettes, a user may depress a plunger to create a vacuum and draw a sample of liquid into a pipette tip. In other examples, the pipette may be automated. In such examples, the automated pipette may be used with a controller (e.g., a computer in an incubator) that controls the strength and duration of the applied pressure.

Unfortunately, presently available pipette tips used with such pipettes (e.g., with the pipettes in the incubator) may introduce contaminants into a liquid. For example, when an unused pipette tip is attached to a previously used pipette to transfer a volume of liquid, because the pipette tip is open at an end adjacent to the pipette, cross contamination may occur between the pipette and the liquid in the pipette tip. In embodiments using presently available pipette tips in a cell culture, this may lower culture efficiency and repeatability. Additionally, because the pipette tips are designed for a single use only, a large volume of waste (e.g., a large pile of used tips) may be amassed, such as during cell culture maintenance.

Applicant has recognized that by providing a pipette tip that may separate a volume of liquid being transferred into the pipette tip from the pipette, various advantages may be Applicant has further recognized that advantages may be realized by providing a pipette tip that may be reusable.

Accordingly, in some aspects, this document relates to a pipette tip having a body defining an inner volume and having first and second ends, the first end arranged to pass liquid into and out of the pipette tip and the second end arranged for attachment to a pipette, and a bladder sealingly attached to the body. In some embodiments, the bladder is disposable within the inner volume. As will be appreciated, in other embodiments, the bladder is not disposable within the inner volume. In some embodiments, the bladder may be placed between the transferred liquid and the pipette. In some embodiments the bladder may extends from a position between the first and second ends of the body toward the first end of the body. For example, the bladder may be attached at the second end and may extend toward the first end of the body, such as when the bladder is in a compressed configuration.

In some embodiments, at least a portion of the inner volume is arranged to accommodate a volume of liquid. In some embodiments, the bladder may be arranged to accommodate a volume of liquid. In some embodiments, the bladder may be expandable to accommodate the volume of liquid.

For purposes herein, being sealingly attached to the body means that the bladder is attached to the body such that a seal is formed at the location where the bladder is attached to the body. For example, the bladder may be heat sealed, glued, bonded, or otherwise suitably attached to the body to create the seal. In some embodiments, the bladder may be attached to the body at a periphery of the bladder. In some embodiments, by being sealingly attached to the body, a volume of transferred liquid may not pass outside of the inner volume at the location where the bladder is attached to the body. In such embodiments, contaminants also may not pass into the inner volume at this attachment location.

For purposes herein, the term "bladder" refers to flexible membrane that is arranged to move (e.g., in response to an applied pressure) to transfer a volume of fluid into and out of the body of the pipette tip body. In some embodiments, the bladder is arranged to accommodate a volume of liquid that is transferred into the inner volume of the pipette tip body. In some embodiments, the bladder may include a membranous sac. The bladder also may include a substantially planar membrane. As will be appreciated, the bladder may have other suitable arrangements in other embodiments.

In some embodiments, the bladder is arranged to move back and forth when pressure is applied to the pipette tip to transfer the volume of liquid. For example, the bladder may be moved in a direction away from the first end of the pipette tip when pressure is applied to the pipette tip to draw a volume of liquid into the inner volume. In some embodiments, the bladder may be moved toward the first end of the body to expel a volume of liquid from the pipette tip. For example, in embodiments in which the bladder moves outside of the body to accommodate the volume of liquid, the bladder may be moved into the body of the pipette tip when the volume of liquid is expelled from the pipette tip.

In some embodiments, the bladder may expand and contract to accommodate a volume of liquid. In such embodiments, the bladder may have a resting volume and an expansion volume, with the bladder expanding from the resting volume to the expansion volume when the pressure is applied to the pipette tip to transfer a volume of liquid into the pipette tip. In some embodiments, the bladder may accommodate a volume of liquid when in the expanded configuration.

In some embodiments, the bladder is disposed within the body in a collapsed or unformed configuration. For example, the membranous sac may be folded into the pipette tip body when the pipette tip is at rest. In such an example, the bladder may expand to form the membranous sac when pressure is applied to the pipette tip. As will be appreciated, in such an example, the bladder may extend between the first and second ends of the body. In other embodiments, the bladder may include a planar membrane that is positioned between the first and second ends but does not extend between the first and second ends while at rest. In some embodiments, the planar membrane may remain substantially perpendicular to a longitudinal axis of the pipette tip. As will be appreciated, in some embodiments, at least a portion of the membrane may extend towards the first end of the pipette tip, such as in response to gravity. In such embodiments, the planar membrane may be moved back and forth in response to an applied pressure to accommodate a volume of liquid. In other embodiments, in response to an applied pressure, the planar membrane may expand and form a membranous sac.

In some embodiments, the bladder is attached to the second end of the body, with the first end of the body arranged to transfer the volume of liquid into and out of the pipette tip. The bladder also may be attached to the first end of the body or to a location in between the first and second ends of the body. In some embodiments, the bladder may be permanently attached or may be removably attached to the pipette body.

In some embodiments, the bladder is arranged to separate the liquid being transferred (e.g., media being transferred from a cell culture vessel) and the pipette or other suitable manipulator arranged to apply a pressure to the pipette tip. In other words, only the bladder and/or the body of the pipette tip may contact the liquid being transferred. As will be appreciated, the extent to which the liquid contacts the bladder depends on the volume of liquid being drawn into the pipette and the pressure being applied to the pipette tip. For example, if only a small volume of liquid is drawn into the pipette, the liquid may only contact the body of the pipette, with the bladder contacting air above the liquid.

In some embodiments, the bladder divides the pipette tip into first and second compartments, the first compartments being in fluid communication with the first end to transfer liquid into and out of the pipette tip and the second compartment being in fluid communication with the second end for receiving an applied pressure, such as a negative pressure. In some embodiments, a first side of the bladder may be exposed to the first chamber and a second side of the bladder may be exposed to the second chamber. In this regard, the first side of the bladder may be exposed to the liquid being transferred into and out of the pipette tip body while the second side of the bladder is exposed to the pipette. In such embodiments, the bladder may reduce or even eliminate cross-contamination between the liquid and the pipette by physically separating the liquid from the pipette. In some embodiments, because the transferred liquid does not contact the pipette and only contacts the bladder and/or the pipette tip body, contaminants may not pass between the pipette (e.g., the piston of the pipette) and the liquid.

As will be appreciated, depending on the material used to form the bladder, it may still be possible for contaminants to pass through the bladder and contaminate the liquid even when the liquid is physically separated from the pipette. As such, according to some aspects, the bladder may be formed of a material that is impermeable to known or possible contaminants. For example, in some embodiments, the bladder is formed of a membrane that is hydrophobic or treated to be hydrophobic. The bladder also may formed of a membrane having a nonporous material or of a material with a porosity less than the size of known or possible contaminants. In some embodiments, the bladder is formed of a material that traps the contaminants in the membrane wall. For example, the membrane may be thick enough to prevent contaminants from reaching the liquid while the pipette is being used, yet still be flexible enough to allow the bladder to be manipulated by the applied pressure.

In some embodiments, the bladder is arranged to separate the liquid from a source of air and/or a vacuum source. As will be appreciated, the bladder also may separate the liquid from other configurations used to apply and remove air to create the vacuum. For example, the liquid transfer system may include a pump, compressed air, valves, membranes or other suitable elements that are separated from the transferred liquid.

In some embodiments, the vacuum source may be created by moving (e.g., removing or supplying) a fluid such as air or liquid. In such embodiments, the pipette may be connected to a liquid supply (e.g., a pump and valve) via one or more fluid conduits. As will be appreciated, other configurations may be used with the pipette tips to create the vacuum. For example, a hand-held pipette may be used, with a plunger being depressed to create a vacuum source. Such a hand-held pipette may have an embedded pump for creating the vacuum.

As described in this document, in response to an applied pressure, a volume of liquid may be transferred into or out of the pipette tip, such as from the culture vessel into the pipette tip and/or from the pipette tip to a cell culture vessel. For purposes herein, being transferred, drawn, and/or expelled into or out of the pipette tip may mean that the volume of liquid is transferred, drawn, and/or expelled into or out of the inner volume of the body of the pipette tip. It also may mean that the volume of liquid is transferred, drawn, or expelled into or out of the bladder (e.g., the stretched membrane) as well as the inner volume.

In some embodiments, the applied pressure is a negative pressure that creates a vacuum that is applied to the bladder. For purpose herein, a negative pressure may mean that there is a negative pressure differential between the air pressure in a container, the pressure of the air in the pipette and/or pipette tip above the bladder, and the air pressure of the environment (e.g., of the atmosphere outside the tip and/or below the bladder). As will be appreciated, the more air that is removed from the pipette and/or pipette tip above the bladder, the greater the vacuum force being applied on the bladder. In some embodiments, the extent of the vacuum (and, thus, the extent of the negative pressure) depends on the surface tension and volumetric weight of the culture media. Accordingly, these additional factors can affect the pressure differential that is required to draw liquid (e.g., the culture media) into the pipette tip.

In some embodiments, in response to the applied negative pressure, e.g., a negative pressure applied via a manipulator, such as a pipette, the bladder is moved outside of the inner volume defined by the body. For purposes herein, being moved outside the body of the pipette tip and/or pipette may mean that the bladder is retracted out of the inner volume defined by the pipette tip body. For example, the bladder may move outwardly beyond a plane extending through the second end of the body. In some embodiments, the bladder is at least partially retracted outside of the body. In such embodiments, when the bladder is retracted in response to the applied negative pressure, a volume of liquid is drawn into the pipette tip. In some embodiments, in response to the applied pressure, a volume of liquid may be drawn into the bladder.

As will be appreciated, the bladder need not extend outside of the body when pressure is applied to the pipette tip to draw a volume of liquid into the inner volume. For example, in embodiments in which the bladder is disposed midway between the first and second ends of the body, the bladder may be extended but not move outwardly beyond the body. As will be further appreciated, although embodiments have been described in which a negative pressure is used to draw the bladder outwardly of the body, in other embodiments, the bladder may be moved inside of the body (e.g., towards the first end of the body) in response to an applied pressure.

In some embodiments, the applied pressure is a positive pressure. As will be appreciated, a positive pressure may mean that there is a positive pressure differential between the air pressure in a container, the pressure of the air in the pipette and/or pipette tip above the bladder, and the air pressure of the environment (e.g., of the atmosphere outside the tip and/or below the bladder). In some embodiments, when the pressure applied to the bladder is greater than the pressure of the environment, the bladder is moved (e.g., pushed or retracted) back into the body to dispense at least a portion of a volume (e.g., a volume of liquid media) from the pipette tip.

In some embodiments, the pipette tip is arranged to accommodate a volume of liquid. In some embodiments, at least a portion of the inner volume of the body may be arranged to accommodate the volume of liquid. As will be appreciated, the portion of the inner volume capable of accommodating a liquid may be defined based on the position of the bladder within the body. For example, if the bladder is positioned at a location midway between the first and second ends, the pipette tip may be arranged to accommodate a volume of liquid that is only about half of the total volume of the inner volume. In some embodiments, the volume of liquid accommodated by the pipette tip, also may include a volume of liquid that the bladder is capable of accommodating. In some embodiments, the volume of the bladder includes a volume enclosed by the membranous sac, such as the expansion volume if the bladders is configured to expand and contract. For example, in some embodiments, the volume of the membranous sac includes the volume that the membrane is stretched from the resting position to the expanded position (e.g., when the membrane is stretched to take on the shape of a bladder). In this regard, the total volume of liquid accommodated by the pipette tip may be less than or equal to a sum of the volume of the inner volume of the pipette tip body and a volume accommodated by the bladder.

In some embodiments, a pipette tip may have a body that can accommodate 1 µL of liquid and a bladder that may accommodate up to about 9 µL. In such a situation, the pipette may be configured to accommodate volumes between about 0 µL and 10 µL of liquid. In some embodiments, the may also be made of an elastic material that allows the bladder to expand and accommodate an even larger volume of liquid. As will be appreciated, in these embodiments, the pipettes may be configured to accommodate a larger range of volumes of liquid than traditional pipettes (e.g., a typical 1 µL pipette tip is limited to volumes between 0 µL and 1 µL).

In some embodiments, the volume of liquid accommodated by the pipette tip is proportional to an amplitude of the pressure differential (e.g., between the air in the container and the environment) and the duration of the applied pressure. For example, applying a greater negative pressure for a longer period of time may draw a larger volume of liquid into the pipette tip than applying a lesser negative pressure to the bladder for the same time period.

In some embodiments, the bladder may be permanently attached to the pipette tip body (e.g., at the second end). The bladder also may be removably attached to the body. For example, the bladder may be snapped into the pipette tip prior to use.

In some embodiments, the liquid transfer device includes a manipulator, such as a pipette, that, in some embodiments, is positioned adjacent the second end of the tip. The tip may be removably attached to the manipulator.

In some embodiments, the pipette includes a pipette shell which is disposed inside the pipette to separate the pipette body from the pipette tip. As will be appreciated, in such embodiments, the pipette shell may further minimize cross contamination between the pipette and the liquid being drawn into the pipette tip. In some embodiments, the pipette shell is disposable. In such embodiments, the pipette shell may be attached to the pipette tip and/or pipette while the liquid is being drawn into the pipette tip and thereafter disposed. In other embodiments, the pipette shell may be reusable. As will be appreciated, in such embodiments, the pipette shell may be sterilized between uses.

In some embodiments, the pipette shell may be discharged from the pipette while still being attached to the pipette tip. In such embodiments, the pipette shell may be used for storing the pipette tip and the liquid drawn into the pipette tip. In some embodiments, a pressure is applied to the pipette tip via the pipette shell. For example, in some embodiments, the pipette shell may have an opening through which pressure (e.g., air or fluid pressure) is applied. In other embodiments, the pipette shell may include a valve for regulating the pressure applied to the pipette tip.

In some embodiments, the liquid transfer system also includes a second pipette tip having a second pipette body defining a volume and having first and second ends, and a bladder sealiningly attached to the body of the second pipette tip. In some embodiments, the bladder is disposable in the inner volume of the second pipette tip. In some embodiments, the bladder may be disposed at a position between the first and second ends, and extend towards the first end (such as when at rest). In such embodiments, the manipulator may be arranged to apply a pressure to the first and/or second bladders to transfer a second volume of liquid into or out of the first and/or second pipette tips, respectively. In some embodiments, the first and second volumes are transferred out of the same culture vessel, although the first and second volumes may be transferred out of different culture vessels (e.g., transferring the first volume of liquid out of a first cell culture vessel and transferring a second volume of liquid out of a second cell culture media).

In some embodiments, the pipette tip is reusable. That is, the pipette may be used to transfer two or more volumes of media containing cells from the same culture vessel prior to disposal. The pipette also may be used to transfer volumes of media from two or more culture vessels. In such embodiments, as will be appreciated, the pipette tip may be sterilized (e.g., via treatment with an antiseptic solution) prior to transferring each sample. The pipette tip also may be disposable such that the tip is only used for a single liquid transfer. In these situations, the pipette tip may be removably attached to the pipette.

In some embodiments, the pipette tip may be used to evaluate the volume of the liquid being transferred into the pipette tip. For example, a sample of the volume of liquid in the pipette tip may be subject to further testing to determine the number of cells in the sample, which could be extrapolated to determine the number of cells in the volume of liquid (or in the culture vessel).

In some embodiments, the pipette tip is used in a cell culture incubator having an incubator cabinet with an internal chamber for incubating cells in one or more cell culture vessels. In such embodiments, the pipette tip may be fluidly coupled to a manipulator that applies a pressure to the bladder (e.g., the formed membranous sac and/or the at rest planar membrane) in the pipette tip body. The manipulator may include one or more pipettes arranged to transfer a volume of media comprising the cells into or out of one or more cell culture vessels within the internal chamber. In some embodiments, the incubator cabinet also has a door opening from an external environment to the internal chamber. An imager may be used to image the cells within the internal chamber. A cell culture vessel transfer device may be used to move one or more cell culture vessels between locations within the internal chamber.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a compressed gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator cabinet), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., barcode readers, cameras, etc.), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

As used herein, an "internal chamber" is a chamber disposed in an incubator cabinet. An internal chamber may include one or more windows (e.g., optical windows made of glass, plastic, composite, or other substantially transparent material for viewing an area inside the incubator cabinet). An internal chamber may include at least one door (e.g., for permitting the transfer of items into or out of the internal chamber). In some embodiments, the at least one door may be disposed between the internal chamber and a transfer chamber. In certain embodiments, an interlock may prevent the door from opening at an undesirable time (e.g., when a portion of the incubator cabinet is open to the surrounding environment so that contaminants cannot enter the internal chamber). An internal chamber may be of any appropriate size and geometry. In some embodiments, an incubator cabinet may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources. In some embodiments, an internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

An internal chamber may be made of any useful material. In some embodiments, an internal chamber may include one or more plastics, polymers, metals, or glasses.

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

A transfer device for moving one or more items may be used to move items between the transfer chamber and the internal chamber. In some embodiments, the transfer device comprises a conveyor belt or other similar device for maneuvering items. Non-limiting examples of items that can be moved by transfer devices include cell culture vessels, pipettes, containers, syringes and other materials and instruments utilized in the culture of cells. In some embodiments, more than one transfer device may be included. In some embodiments, one or more transfer devices are located in the transfer chamber and/or in the internal chamber. In some embodiments, a transfer device may include one or more robotic elements. For example, a transfer device may comprise include one or more robotic arms capable of gripping, lifting, pushing, grabbing, sliding, rotating, translating, releasing, raising, lowering, and/or tilting one or more items (e.g., pipettes).

In some embodiments, the transfer device is a cell culture vessel transfer device. As used herein, a "cell culture vessel transfer device" refers to a device that can transfer one or more cell culture vessels from a first location to a second location. In some embodiments, the transfer device is anchored within the internal chamber. In certain embodiments, the transfer device may transfer one or more items to or from multiple locations in an incubator cabinet. For example, a cell culture vessel transfer device may be used to move a cell culture vessel from a transfer chamber to an internal chamber, and/or from a storage location to an imaging location. In some embodiments, an incubator cabinet includes more than one transfer device for moving one or more items (e.g., separate means for transferring items between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In some cases, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator cabinet (e.g., within a storage array in an internal chamber).

In some embodiments, a cell culture vessel transfer device is an automated transfer device. For example, the automated transfer device may be a robotic arm controlled by a computer that is programmed to move cell culture vessels from a storage location within the internal chamber of the incubator to an imaging location within the internal chamber of the incubator. In some embodiments, a cell culture vessel transfer device is manually operated. For example, a robotic arm located inside the internal chamber of an incubator may be operated by a user-controlled joystick from a location outside of the internal chamber of the incubator in order to move cell culture vessels from a storage location within the internal chamber of the incubator to an imaging location within the internal chamber of the incubator.

As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. Non-limiting examples of cell culture vessels include flasks, suspension culture flasks, spinner flasks, plates, petri dishes and/or bags. In certain embodiments, a cell culture vessel includes a transparent or optically clear window. For example, a lid coupled to the housing of a cell culture vessel may include an optically clear portion for viewing cells e.g., with a microscope or other imager. In some embodiments, a cell culture vessel includes one or more portions that are substantially non-reflective. In some embodiments, the cell culture vessel is barcoded. Therefore, in some embodiments, the incubator includes a barcode reader.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

As used herein, a "storage location" refers to a location at which one or more cell culture vessels is stored (e.g., within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that are molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device camera or CMOS camera), apertures, mirrors, light sources (e.g., a laser or lamp), or other optical elements. An imager may be a microscope. In some embodiments, the imager is a brightfield microscope. In other embodiments, the imager is a holographic imager or microscope. In other embodiments, the imager is a fluorescence imager or microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator cabinet provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

In some embodiments, a cell culture vessel is substantially aligned with an imager. In some embodiments, a cell culture vessel is substantially aligned with an imager via the use of at least one fiducial mark. As used herein, the term "substantially aligned" implies that one or more elements are substantially overlapping, identical, and/or in line with one another. The substantial alignment of one or more cell culture vessels at one or more locations (e.g., imaging locations) may facilitate the analysis of a sample by permitting overlapping images of the cell culture vessel to be obtained. For example, a cell culture vessel may be imaged at a first imaging location by a first imager and subsequently imaged at a second imaging location by a second imager. If the imaging fields of the respective imagers are substantially aligned, the images recorded by the first and second imagers may be combined ("stitched together") for analysis. One or more fiducial marks present on one or more cell culture vessels may facilitate substantial alignment. In some cases, one or more fiducial marks present at one or more imaging or other locations (e.g., manipulation or maintenance locations) may facilitate substantial alignment.

As used herein, a "manipulator for manipulating cells" refers to a device for manipulating cells in the internal chamber. The manipulator may include one or more needles, capillaries, pipettes, and/or micromanipulators. For example, the manipulator may include a cell picker. A manipulator for manipulating cells may operate by detecting desirable cells or groups thereof present at a first location based on a predetermined criterion and transferring the desired cells or groups thereof from the first location to a second location. A cell picker may detect, pick, and/or transfer desirable or undesirable (e.g., pre-differentiated cell weeding) cells or groups thereof based on a manual or automated analysis. In some embodiments, information produced by an imager may be analyzed to detect desirable or undesirable cells. The cell picker may then transfer the desirable or undesirable cells to the second location. For example, an imager may image cells in or on a cell culture vessel at an imaging location, and the image used to identify desirable or undesirable cells or groups thereof. The cell picker may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the first location of the cells may be in or on a cell culture vessel. In particular embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, the manipulator includes at least one microelectrode. As used herein, the term "microelectrode" refers to an electrical conductor used to deliver electrical stimulation to a cell. For example, microelectrodes can be used to deliver genetic material into a cell by electroporation. In some embodiments, the manipulator includes at least one microinjector. Generally, microinjectors are glass micropipettes that have been pulled to form a sharp, hollow structure capable of piercing the membrane of a cell and serving as a conduit for the introduction of genetic material into the cell.

In some embodiments, a manipulator is manually operated. For example, a manipulator having a cell picker located inside the internal chamber of an incubator cabinet may be electronically-linked to and controlled by a user-directed joystick located outside the internal chamber of the incubator cabinet. In some embodiments, the user-directed joystick is connected to a display device. In some embodiments, the display device shows images captured by an imaging device inside the internal chamber of the incubator cabinet.

In some embodiments, a manipulator is automated. For example, a manipulator inside an internal chamber of an incubator cabinet may be electronically connected to a controller outside of the incubator cabinet, which is electronically connected to a computer that directs the manipulator. For example, the controller may instruct the manipulator to apply a vacuum to one or more pipette tips fluidly connected to the manipulator.

One or more elements of the manipulator for manipulating cells may be sterilized, for example using a sterilizing composition or method (e.g., ethanol or ozone gas, UV Light, Hydrogen peroxide), prior to manipulation.

As used herein, "manipulation location" refers to the location at which cells are manipulated by a manipulator for manipulating cells (e.g., a cell picker). In certain embodiments, the manipulation location may be the same as the imaging location.

According to one aspect, the cell culture incubator includes an incubator cabinet with an imaging location and a manipulating location. Cells of a cell culture vessel are imaged at the imaging location by an imager and manipulated at the manipulating location by a manipulator. In some embodiments, the imaging location and the manipulating location are two distinct locations within the incubator cabinet. The cell culture incubator may include a transfer device that moves cell culture vessels between the imaging location and the storage location. In other embodiments, the imaging location and the manipulating location are the same, such that the cells of culture vessels are imaged at the manipulation location.

In some embodiments, an imager may be used in conjunction with a manipulator. For example, an imager may image cells in or on a cell culture vessel at an imaging location, and the image used to identify desirable cells or groups thereof. The cell picker, which may or may not be resident at the imaging location, may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, a single location within the incubator cabinet may serve as an imaging location and a manipulating location. In one embodiment, cells are imaged as they are manipulated by the manipulator. In some embodiments, the imaging location and imaging location may be at separate locations within the incubator cabinet.

In some embodiments, the manipulator includes sensors that allow it to report its position and determine when it has touched the bottom of the cell culture vessel. In some embodiments, an imager may be used to guide the manipulator in order to achieve repeatability and accuracy. In some embodiments, compliance (e.g., springiness) in the manipulator may be used to relax the need for extreme mechanical accuracy.

In some embodiments, one or more manipulators are used to manipulate one or more pipettes as described in this document. In some embodiments, manipulators are used to place and/or remove pipette tips on the pipettes.

Figure 1:
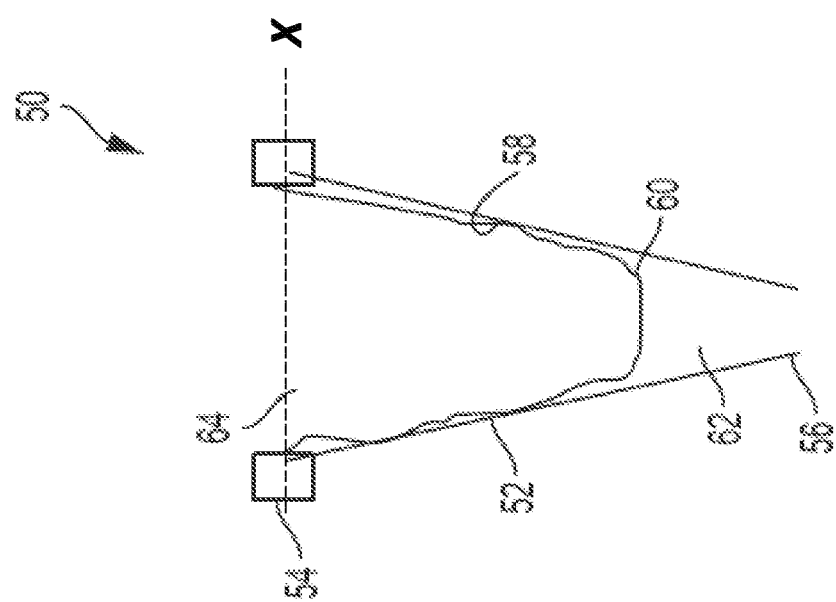

Turning now to the figures, FIG. 1 illustrates a pipette tip (50) according to one aspect of the present document. As shown in this figure, the pipette tip (50) includes a body (52) defining an inner volume and having first and second ends (56, 54). The pipette tip (50) also includes a bladder (58) disposed within the inner volume of the body (52). In this embodiment, the bladder (58) is defined by a membranous sac, formed by a membrane (60), that extends towards the first end (56). In some embodiments, the second end (54) of the pipette tip (50) is arranged to be attached (e.g., removably attached) to a pipette (see FIG. 5). In some embodiments, the first end (56) is the exit end of the body (52). In such embodiment, the first end (56) may be configured to transfer a volume of liquid into and out of the pipette tip (50), such as into and out of the inner volume of the body (52).

In some embodiments, as shown in FIG. 2, the bladder (58) may be defined by a planar membrane (60) that is substantially perpendicular to a longitudinal axis A of the pipette tip (50). As will be appreciated, in some embodiments, at least a portion of the membrane (60) may extend towards the first end (56) of the body in response to gravity. In some embodiments, in response to an applied pressure, the planar membrane (60) may move back and forth. In some embodiments, in response to the applied pressure, the planar membrane (60) may expand and contract. For example, the bladder (58) may expand from the planar membrane (60) shown in FIG. 2 to the membranous sac shown in FIG. 1.

Turning back to FIG. 1, in some embodiments, the bladder (58) may be attached to the second end (54) of the body (52) and extend towards the first end (56) of the body. In such embodiments, the bladder (58) may be attached to the body (52) at a periphery of the bladder (58). In some embodiments, the bladder may be sealingly attached to the body (52) such that a fluid tight seal is formed between the body (52) and the bladder (58). In such embodiments, as will be described, liquid may not travel beyond the bladder, at the location where the bladder is attached to the body, and contaminants may not travel into the inner volume.

Figure 3B:
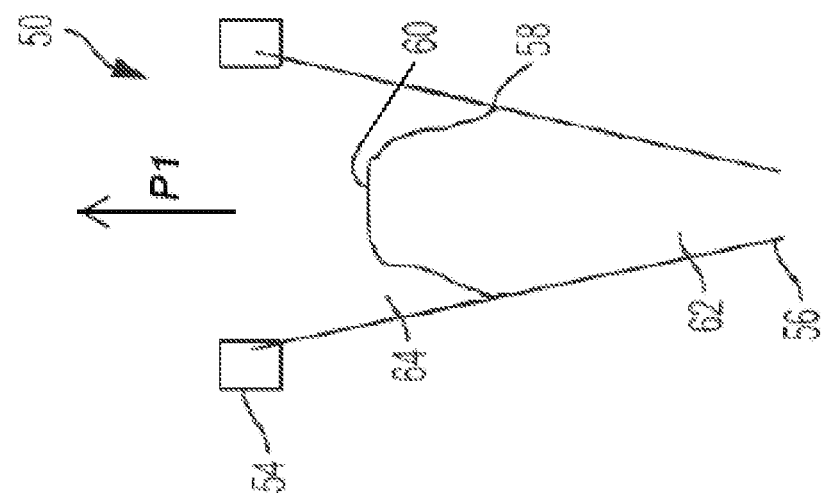
FIG. 3B is a schematic illustration of the pipette tip of FIG. 3A, with a bladder in an extended configuration.
Figure 3A:
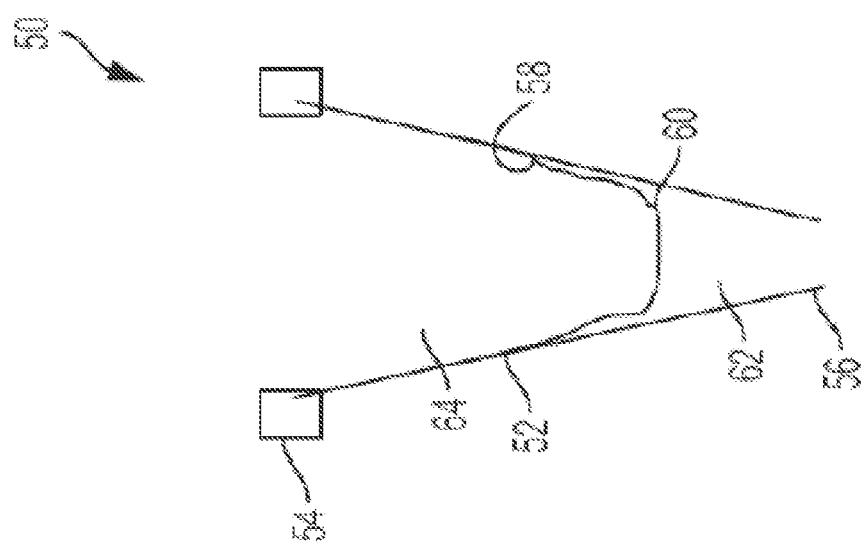
FIG. 3A is a schematic cross-sectional side view of a pipette tip according to one embodiment.
Figure 4B:
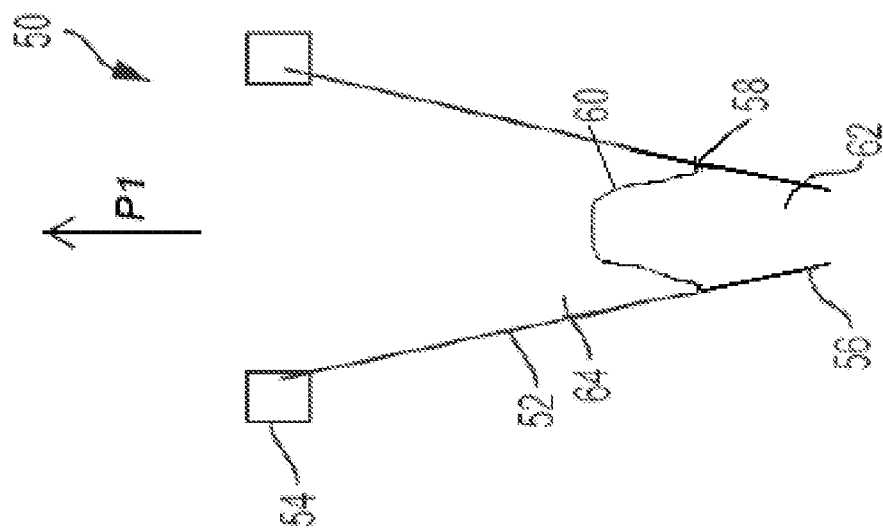
FIG. 4B is a schematic cross-sectional side view of the pipette tip of FIG. 4A, with a bladder in an extended configuration.
Figure 4A:
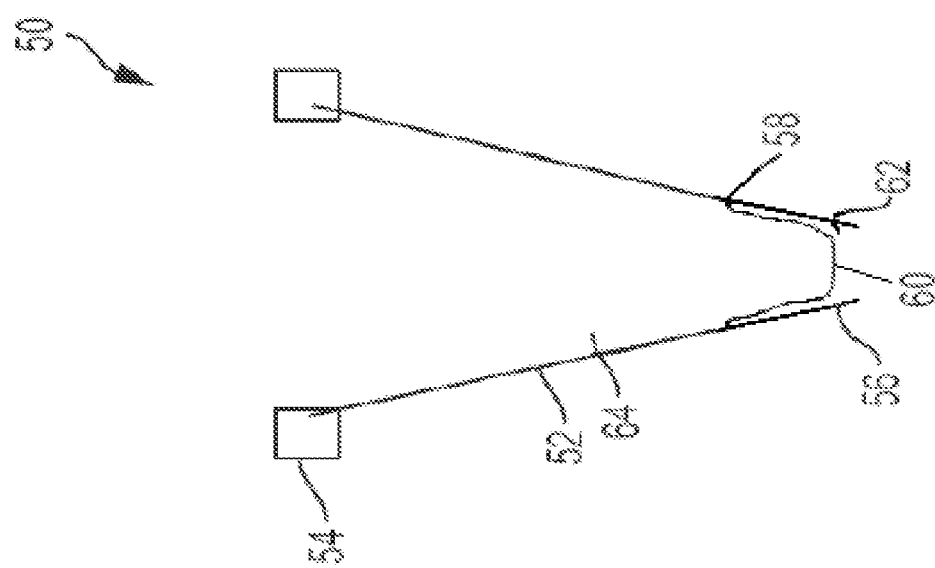
FIG. 4A is a schematic cross-sectional side view of a pipette tip according to another embodiment.

As will be appreciated, although the bladder (58) is attached to the second end (54) in the embodiment shown in FIG. 1, in other embodiments, the bladder (58) may be attached to another suitable location of the body. For example, as shown in FIGS. 2 and 3A, the bladder (58) may be attached to a location in between the first and second ends (56, 54) of the body (52). As shown in FIG. 3A, the bladder (58) may still extend towards a first end (56) of the body (52). In some embodiments, the bladder (58) may extend only part of the way toward the first end (56) of the body, while in other embodiments, the bladder may extend to a position at or near the first end (56) of the body. As shown in FIG. 4A, in still another embodiment, the bladder (58) may be attached at or near the first end (56) of the body (52).

Figure 5E:
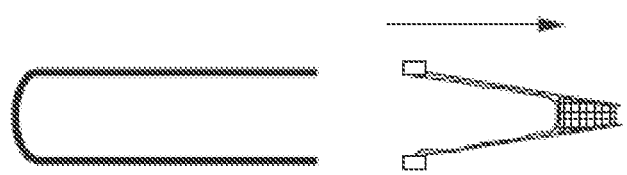
FIG. 5A-FIG. 5E are schematic illustrations of a volume of liquid being transferred into and out of a pipette tip attached to a pipette.
Figures 5C, 5D:
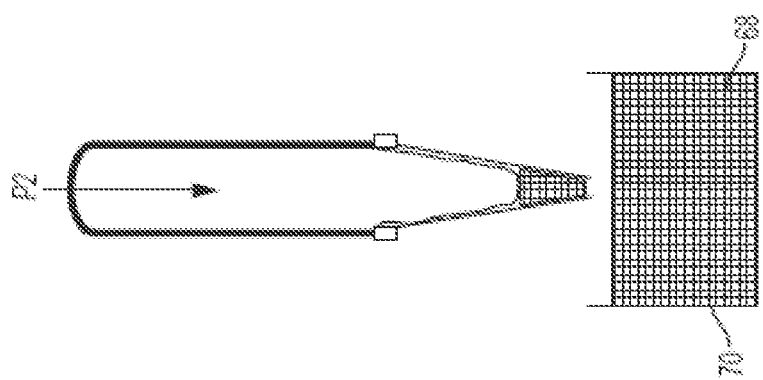

In some embodiments, as shown in FIG. 1-FIG. 4A, the bladder (58) divides the body (52) into two chambers (62, 64). In such embodiments, the first chamber (62) is in fluid communication with the first end (56) of the pipette tip, e.g., where the liquid is transferred into and out of the body, and the second chamber (64) is in fluid communication with the second end of the body (54). The second chamber (64) also may be in fluid communication with a pipette (see, e.g., FIG. 5A) for receiving an applied pressure (e.g., a negative pressure, as described in this document). In such embodiments, a first side of the bladder may be exposed to the transferred liquid while a second, opposite side of the bladder may be exposed to the pipette. In this regard, the bladder (58) may separate the pipette from the transferred liquid. As shown in FIG. 5C, for example, the bladder may separate the culture media transferred into the pipette tip from the pipette (66). Such separation may reduce or even eliminate contamination between the pipette and the media in such embodiments In some embodiments, the bladder (58) is permanently attached to the body (52) of the pipette tip (50). In such embodiments, the bladder (58) may be bonded, glued, fastened, or otherwise attached, to the pipette tip. The bladder (58) also may be ultrasonically welded to the pipette tip. In other embodiments, the bladder (58) may be removably attachable to the pipette tip (50). For example, the bladder (58) may be snapped onto the body (52) of the pipette tip (50) prior to use (e.g., prior to transferring the volume of liquid into or out of the pipette tip). As will be appreciated in view of the above, such attachment methods may form a fluid tight seal between the bladder and the body.

In some embodiments, the bladder (58) is formed of a membrane made of a strong yet flexible material. For example, in some embodiments, the bladder (58) may be arranged to expand and contract to accommodate the volume of liquid. The bladder (58) also may be moved between a position inside of the body to a position outside of the body to accommodate the volume of liquid. In some embodiments, the bladder (58) may have elastomeric properties. The bladder (58) also may be formed of a membrane (60) made of organic and/or inorganic materials. In some embodiments, the bladder (58) includes a polymeric structure. In some embodiments, the bladder (58) includes a latex material. In some embodiments, the bladder (58) is arranged to retain the liquid within the bladder (58). In such embodiments, the bladder may be formed of a membrane (60) that is non-porous and/or liquid impermeable. For example, the membrane may be made of a hydrophobic material or may be treated to be hydrophobic. As will be appreciated, such characteristics of the membrane may prevent the transferred liquid from passing from the pipette tip into the pipette, which may contaminate the pipette (and future samples).

In some embodiments, the bladder (60) may include a smooth surface. In some embodiments, the bladder (58) does not include folds, while in other embodiments, the bladder may include folds.

In some embodiments, as shown in FIG. 1, the bladder (58) may include a convex configuration when the bladder is at rest (e.g., there is no applied pressure). In such embodiments, the bladder may have a curved configuration below a plane X that extends through the periphery of the bladder. In some embodiments, at least a portion of bladder may move on the other side of the plane X in response to an applied pressure. In some embodiments, the bladder may take on a concave configuration above the plane X in response to an applied pressure.

In some embodiments, the pipette tip (50) is configured to transfer a range of volumes of a liquid (e.g., from about 1 μL to about 10 mL, or more, of liquid). For example, the pipette tip (50) may be configured to transfer culture media between a culture vessel and the pipette tip and back to the culture vessel or to another culture vessel. As will be appreciated, a manipulator, such as a pipette (66) (see FIG. 5A), may be configured to apply a pressure to the pipette tip to transfer the desired volume(s) of liquid into and out of the pipette tip. In some embodiments, a controller may be programmed to instruct the pipette (66) transfer the desired volume(s) of liquid into the pipette tip.

As will be appreciated, in these examples, the volume of liquid accommodated by the pipette tip is proportional to the pressure applied to the bladder. That is, the volume of liquid drawn into (or dispensed out of) the pipette tip is dependent on the amplitude of the pressure differential (e.g., between air in the container and the environment) and the duration of the applied pressure. For example, applying a greater negative pressure for a longer period of time will draw a larger volume of liquid into the pipette tip than applying a lesser negative pressure to the bladder for the same time period. As such, in these embodiments, the pipette (66) may be instructed (e.g., via human intervention or via a controller) to apply a pressure to the bladder for the period of time corresponding to the desired volume of liquid.

In some embodiments, the bladder (58) and/or pipette tip (50) may comprise a plastic material. For example, the bladder (58) may include a polyurethane and/or silicone material. In one embodiment, the pipette tip (50) comprises a polycarbonate, polypropylene, polyethylene, and polystyrene material, although other suitable materials may be used. In some embodiments, as shown in FIG. 1, the pipette tip (50) may have a frusto conical shape, although other suitable shapes may be used (e.g., a cylindrical shape).

Figure 5B:
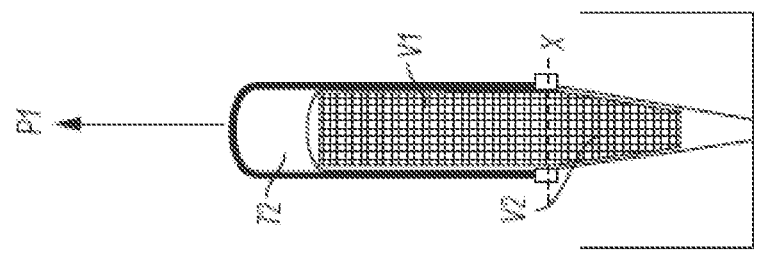
Figure 5A:
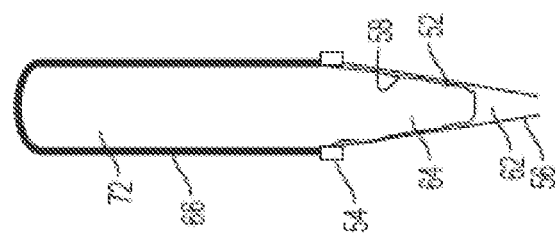

FIGS. 5A-5E illustrate embodiments of the pipette tip (50) being used to transfer a volume of liquid, such as a volume of media containing cells (68), into and out of the pipette tip (50). FIG. 5A shows the pipette tip (50) attached to a pipette (66). As shown in this figure, the bladder (58) has divided the pipette tip into two chambers (62, 64), with the first chamber (62) being in fluid communication with the first end (56) of the body (52) and the second chamber (64) being in fluid communication with the second end (54) of the body and with the pipette (66). In this regard, the bladder may separate the media culture from the pipette.

As shown in FIGS. 5C-5D, in some embodiments, the second chamber (64) is arranged to receive first and second applied pressures to transfer a volume of liquid into and out of the pipette tip (50), respectively. To begin transferring a volume of liquid into the pipette tip (50), as shown in FIG. 5B, the first end (56) of the pipette tip 50 is inserted into media (68) containing cells stored in a culture vessel (70). As shown in FIGS. 5A and 5B, when the pipette tip (50) is first attached to the pipette (66) and no pressure has been applied to the bladder (58), the bladder (58) is disposed inside of the body (52) and extends from the second end (54) towards the first end (56). As with other embodiments, in this at-rest position, the bladder extends below the plane X extending through the periphery. As shown in FIG. 5C, when a first pressure P1 is applied to the bladder, the bladder (58) is retracted in a direction away from the first end (56) of the pipette tip (50) (see arrow), thus drawing the media 68) into the pipette tip (50). In this arrangement, at least a portion of the bladder is moved on the other side of the plane X As shown in FIG. 5C, in response to the applied pressure, the media (68) has been drawn in to the body (52) and into the bladder (58) of the pipette tip (50). As will be appreciated, in other embodiments, the media (68) may be drawn into only one of the bladder (58) and the body (52). As described in this document, the level of media drawn into the pipette tip body (52) and/or bladder (58) depends on the applied pressure and the duration of applied pressure.

In some embodiments, the first pressure P1 applied to the bladder (58) may be a negative pressure. As described in this document, such a negative pressure may create a vacuum that is applied to the bladder (58), thus causing the bladder (58) to retract out of the body (52) to draw the media (68) into the pipette tip (50).

As shown in FIG. 5C, in some embodiments, the bladder (58) may be been completely retracted out of the body (52) of the pipette tip (50) and into a body (72) of the pipette (66). In other embodiments, the bladder (58) may be only partially retracted into the pipette body (72). In still other embodiments, as shown in FIGS. 3B and 4B, the bladder need not be retracted out of the pipette tip body when a pressure is applied. As will be appreciated, the movement of the bladder with respect to the body of the pipette tip may be determined based on the position in which the bladder is attached to the body of the pipette tip, the size and stretchability of the bladder, and the applied pressure. For example, a substantially planar membrane may be attached at the second end of the pipette tip body but not be moveable out of the pipette tip body (e.g., beyond the plane extending through the second end of the pipette tip body. In other embodiments, as shown in FIGS. 3A and 3B, the bladder may be positioned midway between the first and second ends. In such embodiments, even with the bladder moving and/or expanding, the bladder does not move out of the inner volume of the pipette tip. As will be appreciated, in embodiments in which the bladder is attached at the first end of the pipette tip body, the bladder may extend outwardly beyond the first end of the pipette tip body when the bladder is in an at-rest position.

Turning back to FIG. 5C, in embodiments in which the bladder is retracted out of the pipette tip body, the bladder may be arranged to accommodate a volume of liquid. In such embodiments, the volume of accommodated liquid in the bladder may be less than or equal to the volume V1 of the bladder. The exact volume of accommodated liquid in the bladder may vary depending on the pressure exerted on the pipette tip and the amount to which the bladder is extracted outwardly beyond the pipette tip body.

As described in this document, the pipette tip (50) may be configured to accommodate a volume of liquid. In some embodiments, as shown in FIG. 5C, the volume of accommodated liquid may be less than or equal to a sum of the volume V1 of the bladder (58) and a volume V2 of the body (52) of the pipette tip (50). For purposes herein, the volume of the body of the pipette tip (50) is defined as the volume of between the first end (56) of the body (52) and the location where the bladder (58) is attached to the body (see, e.g., the line labeled X, a plane extending through the periphery of the bladder). As will be appreciated, in the embodiment shown in FIG. 5C, where the bladder (58) is attached at the second end (54) of the body, the volume V2 of the body is defined as the volume between the first and second ends (56, 54). In embodiments in which the bladder is attached in between the first and second ends (56, 54), however, the volume may be defined as a volume between the first end a the plane extending through the periphery of the bladder, at an intermediate location. For purposes herein, the volume of the bladder is defined as the volume enclosed by the membrane (60) attached to the body (52). That is, the volume of the bladder (58) may include the volume between the membrane (60) in the moved/expanded configuration and the location to which the bladder is attached to the body (e.g., the plane extending through the periphery).

As will be appreciated, the volume of media (68) drawn into the pipette tip (50) need not fill the entire volume defined by the sum of the volumes of the bladder and the pipette tip body. Thus, the volume of the liquid may be less than the sum of the volume of the body and the volume of the bladder in some embodiments. In some embodiments, however, the entire volume may be accommodated by the media.

Once the media (68) has been transferred into the pipette tip (50), the media (68) may then be transferred out of the pipette tip (50) and back to the same culture vessel (70). The media (68) also may be transferred to a another culture vessel (70). In either situation, as shown in FIG. 5D, a second pressure P2 may be applied to the bladder to move the bladder towards the first end (56) of the body (52) (see arrow), thus expelling the media from the pipette tip. As will be appreciated, the entire volume of media need not be expelled from the pipette tip.

In embodiments in which additional liquid transfers are to be performed via the pipette (66), the steps shown in FIGS. 5B-5D may be repeated with the same pipette tip (50) and culture vessel (70). Once the transfer(s) have been finished, the pipette tip (50) may be removed from the pipette (66), as shown in FIG. 5E. In embodiments in which the pipette tip (50) is reused with different culture vessels, the pipette tip (50) may be sterilized prior to repeating the steps shown in FIGS. 5B-5D with the new culture vessel. As will be appreciated, the pipette tip (50) also may be disposed after each liquid transfer, with a fresh pipette tip (50) being attached to the pipette (66).

As will be appreciated, although embodiments are shown and described for transferring a fluids, such as a culture media, the pipette tips may be used to transfer other types of fluids (e.g., air or water).

In some embodiments, the pipette tip (50) is removed from the pipette (66) by pulling the pipette tip (50) away from the pipette (66), (see the arrow in FIG. 5E). In other embodiments, the pipette (66) may have an ejection button (not shown) to eject the pipette tip (50) from the pipette (66).

As will be appreciated, although the embodiments shown in FIGS. 5A-5E illustrate a bladder (58) being moved (e.g., retracted) into and out of the pipette tip, in other embodiments, the first and second pressures P1, P2 may be used to expand and contract the bladder to draw in and dispense the liquid from the bladder. In such embodiments, the bladder may be expanded into the body (72) of the pipette (66).

As will be further appreciated, although the embodiments shown in FIGS. 5A-5E include a bladder defined by a membranous sac, the same steps may be repeated with a pipette tip (50) having a bladder (58) defined by a planar membrane. In such an embodiment, the first pressure P1 may be used to move the membrane back and forth. In other embodiments, the first pressure P1 may be used to stretch the planar membrane into the membranous sac, which is thereafter used to accommodate the volume of liquid. In such embodiments, the second pressure P2 also may be used to move the stretched bladder back into the body of the pipette tip (50) to dispense the liquid from the pipette tip (50) and return the membranous sac to the planar membrane configuration.

Figure 6A:
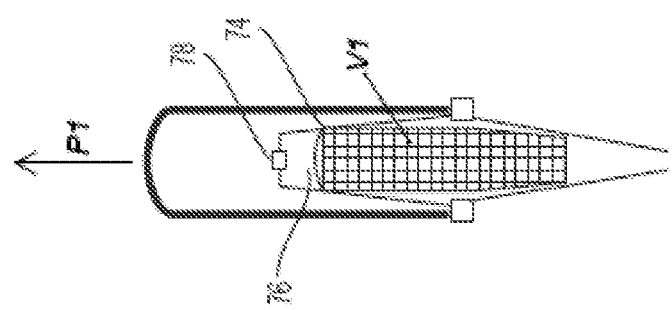
FIGS. 6A and 6B are schematic illustrations of a volume of liquid being transferred into a pipette tip attached to a pipette with a pipette shell.
Figure 6B:
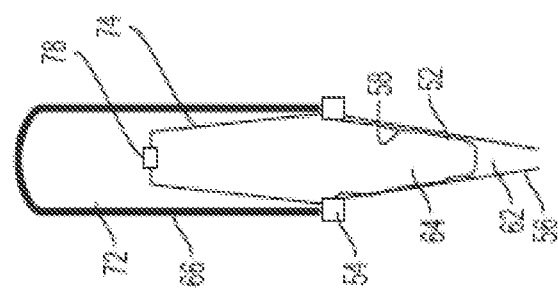

Although FIGS. 5A-5E show the pipette tip (50) being attached directly to the pipette (66), with the bladder (58) being retractable into the body (72) of the pipette (66), in other embodiments, the pipette tip (50) may be further separated from the pipette (66). For example, as shown in FIG. 6A, the pipette may include a pipette shell (74) that is disposed within the body (72) of the pipette (66) and arranged to receive the bladder (58) in response to an applied pressure. In such an embodiment, as shown in FIG. 6B, the pipette shell (74) may include a body (76) into which the bladder (58) is retracted in response to the first pressure P1. As with the pipette body (72), the body (76) of the pipette shell (74) may be greater than or equal to the volume V1 of the bladder (58). In some embodiments, the pipette shell (74) is removably attachable to the pipette (66) and/or the pipette tip (50). For example, the pipette shell (74) may be attached to the pipette (66) and/or pipette tip (50) prior to attaching the pipette tip (50) to the pipette (66) and drawing a volume of liquid into the pipette tip (50).

In some embodiments, the pipette tip (50) may be separated from the pipette shell (74) after the liquid has been drawn into and out of the pipette tip (50). In other embodiments, the pipette shell (74) may remain attached to the pipette tip (50) after the pipette tip (50) has drawn the liquid into the pipette tip (50). In such embodiments, the liquid sample may be stored with the pipette tip. For example, the pipette shell (74) may be arranged to maintain the pressure applied to the pipette tip (50) after the pipette tip (50) has been separated from pipette (66) so that the pipette tip (50) may be stored in an upright position. In embodiments in which the applied pressure is lost once the pipette tip has been separated from the pipette, the pipette tip (50) and pipette shell (74) may be inverted, with pipette shell (74) serving as storage for the retracted bladder (with the liquid sample). In some embodiments, a cover (not shown) may be attached to the pipette tip (50) for storing the liquid sample.

In some embodiments, the pipette shell (74) includes a pressure applicator (78) that is configured to allow the pressure to be applied to the pipette tip (e.g., via the pipette (66)). In some embodiments, the pressure applicator (78) includes an opening in the pipette shell (74) through with the pressure may be applied to the bladder. In other embodiments, the pressure applicator (78) may include a valve for regulating the applied pressure (e.g., a negative pressure) to the bladder.

In some embodiments, the pipette shell may be made of a similar material as the pipette tip and bladder. For example, the pipette shell may be made of a plastic material. As will be appreciated, the pipette shell may be made of a rigid material, thus allowing the pipette shell to rest stably on a surface after an attached pipette tip and pipette shell are inverted.

In such embodiments, the pipette shell (74) may be disposable, although the pipette shell (74) also may be reusable. In embodiments in which the pipette shell is reusable, the pipette shell may be sterilized in between uses.

Figure 7:
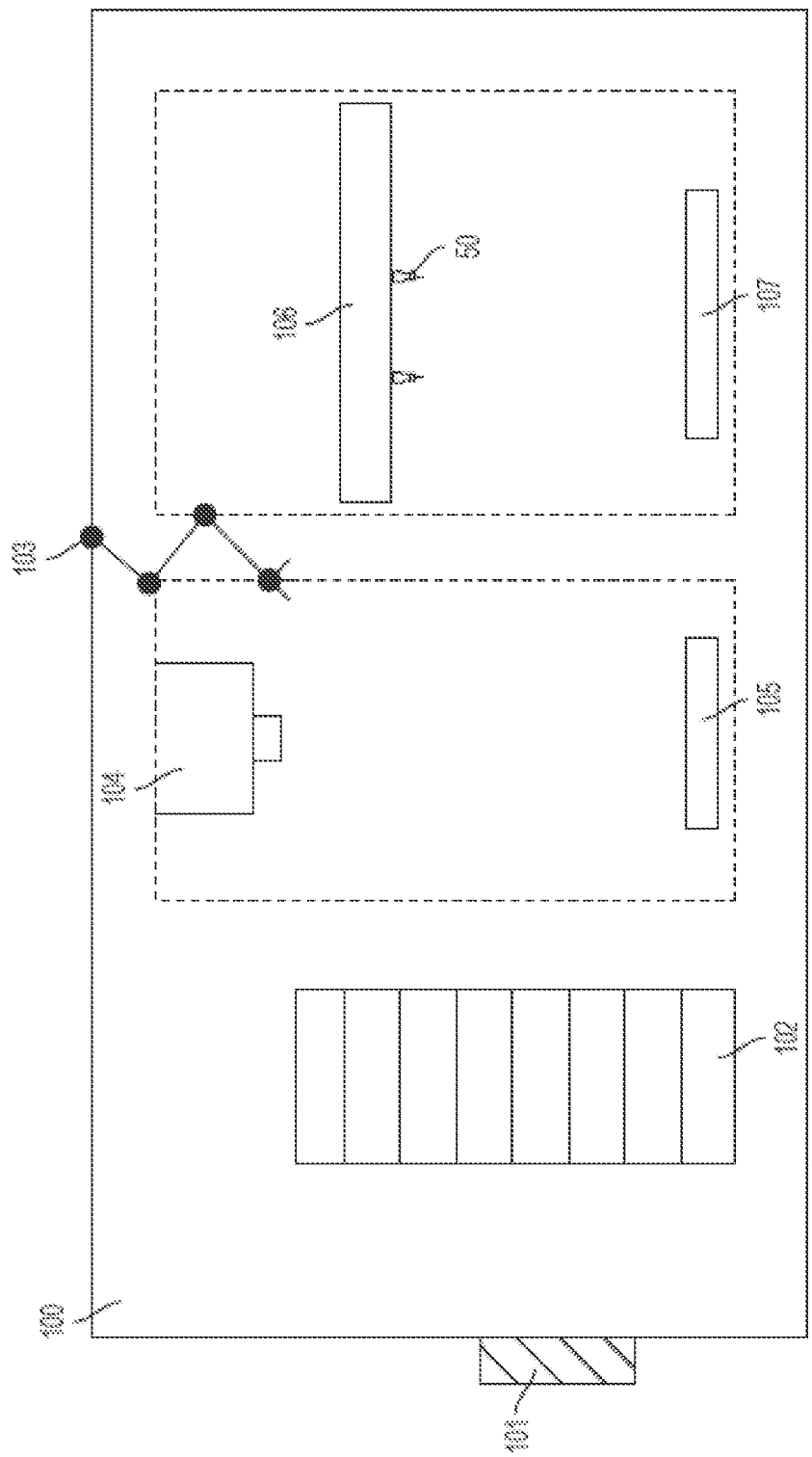
FIG. 7 is a schematic of an illustrative embodiment of a cell culture incubator having an imager, a manipulator, and a pipette tip.

FIG. 7 illustrates an embodiment in which the pipette tip (50) is used in a cell culture incubator. The cell culture incubator includes an incubator cabinet having an internal chamber (100) for incubation of cells in one or more cell culture vessels. The incubator cabinet includes an external door (101) that opens and closes to permit communication between an external environment and the incubator cabinet. In some embodiments, the external door opens and closes to permit communication between an external environment and the internal chamber. The internal chamber is configured to hold one or more cell culture vessels. The one or more cell culture vessels are stored in a storage location (102). In some embodiments, the storage location is a free-standing structure. For example, a storage location may be a test tube or culture flask rack that can be removed from the internal chamber of the incubator for loading and unloading of culture vessels. In some embodiments, the storage location is affixed to a surface of the internal chamber. For example, the storage location may be a series of racks or shelves that are connected to the walls or floor of the internal chamber and are thus not able to be removed from the incubator cabinet.

In some embodiments, the cell culture incubator includes a cell culture vessel transfer device (103) for moving one or more cell culture vessels. The cell culture transfer device may be affixed to any appropriate surface of the internal chamber of the incubator. For example, the cell culture vessel transfer device may be affixed to the top or ceiling of the internal chamber. Alternatively, the cell culture vessel transfer device may be affixed to a side wall of the internal chamber. In some embodiments, the cell culture vessel transfer device is not affixed to the wall of the internal chamber. For example, the cell culture vessel transfer device may rest on a wheeled tripod or other mobile structure that can be moved around the internal chamber.

In some embodiments, the transfer device moves one or more cell culture vessels from a storage location (102) to an imaging location (105) or to a manipulation location (107). The transfer device (103) can also move one or more cell culture vessels from an imaging location (105) to a manipulation location (107) or from a manipulation location (107) to an imaging location (105). When imaging or manipulation are complete, the transfer device (103) moves one or more cell culture vessels from an imaging location (105) or a manipulation location (107) to a storage location (102).

In some embodiments, the incubator cabinet includes a first imaging location (105) and a manipulation location (107). In some embodiments, one or more imaging locations are located on a surface of the internal chamber opposite from an imager. In some embodiments, imaging locations are platforms, either free-standing or affixed to a surface of the internal chamber. In some embodiments, the platform is movable. For example, a movable platform may be affixed to two or more rods that allow the platform to be moved left, right, forward, backward, up or down in relation to an imager. In some embodiments, the movable platform is motorized.

In some embodiments, the incubator cabinet includes a first imager (104) that images the cells of cell culture vessels when the vessels are at the first imaging location (105). In some embodiments, the first imager is a bright-field microscope. In some embodiments, the first imager is a holographic microscope.

In some embodiments, a manipulator (106) manipulates the cells of cell culture vessels when the vessels are at the manipulation location (107). In some embodiments, the manipulator has an array of needles, capillaries, pipettes, and/or micromanipulators. For example, the manipulator may include a cell picker. In some embodiments, a manipulator has a cell picker. Generally, manipulation locations share many characteristics with imaging locations, as described herein.

As shown in FIG. 7, the manipulator (106) may be in fluid communication with two of the disclosed pipette tips (50) for transferring a volume of media containing cells into and out of the pipette tips (50). As will be appreciated, the manipulator (106) may be in fluid communication with only one pipette tip in some embodiments or with three or more pipette tips in other embodiments. In some embodiments, the manipulator may be in fluid communication with an array of pipette tips. In such embodiments, the manipulator may apply first and second pressures to manipulate the bladder (e.g., move, retract, expand, contract or stretch).

Figure 8:
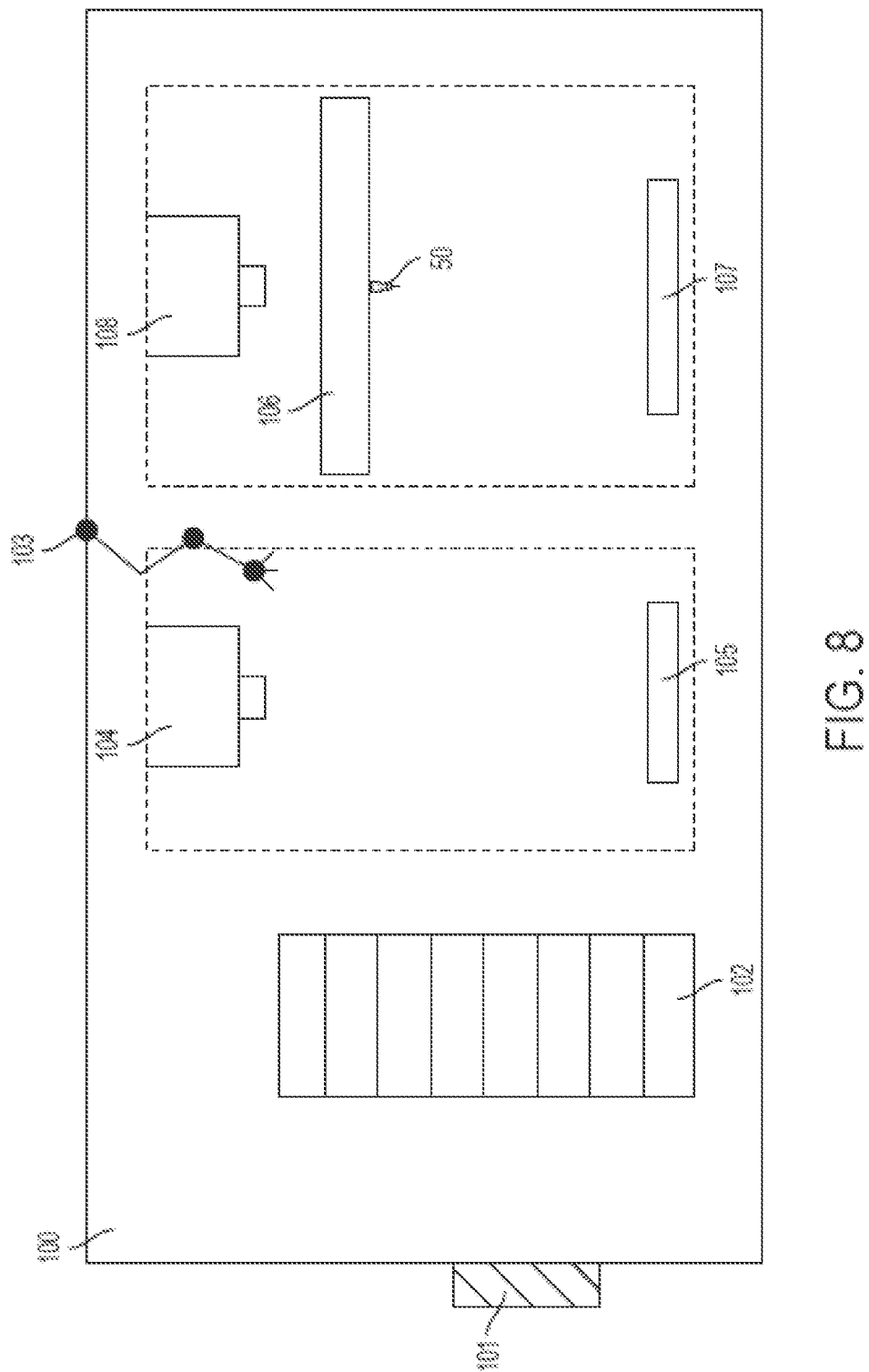
FIGS. 8-9 are schematics of illustrative embodiments of cell culture incubators, with FIG. 8 showing a schematic of a cell culture incubator having a second imager and FIG. 6 showing a schematic of a cell culture incubator, wherein the imaging location and the manipulating location are the same location.

FIG. 8 depicts another illustrative embodiment of a cell culture incubator. In some embodiments, the incubator cabinet has a second imager (108). The second imaging location may be at or near the manipulation location (107). In some embodiments, the second imaging location and the manipulation location (107) are the same location. In some embodiments, a second imager (108) images the cells of cell culture vessels while the cells are manipulated by the manipulator (106). In some embodiments, the second imager is a bright-field microscope. In some embodiments, the second imager is a holographic microscope.

Figure 9:
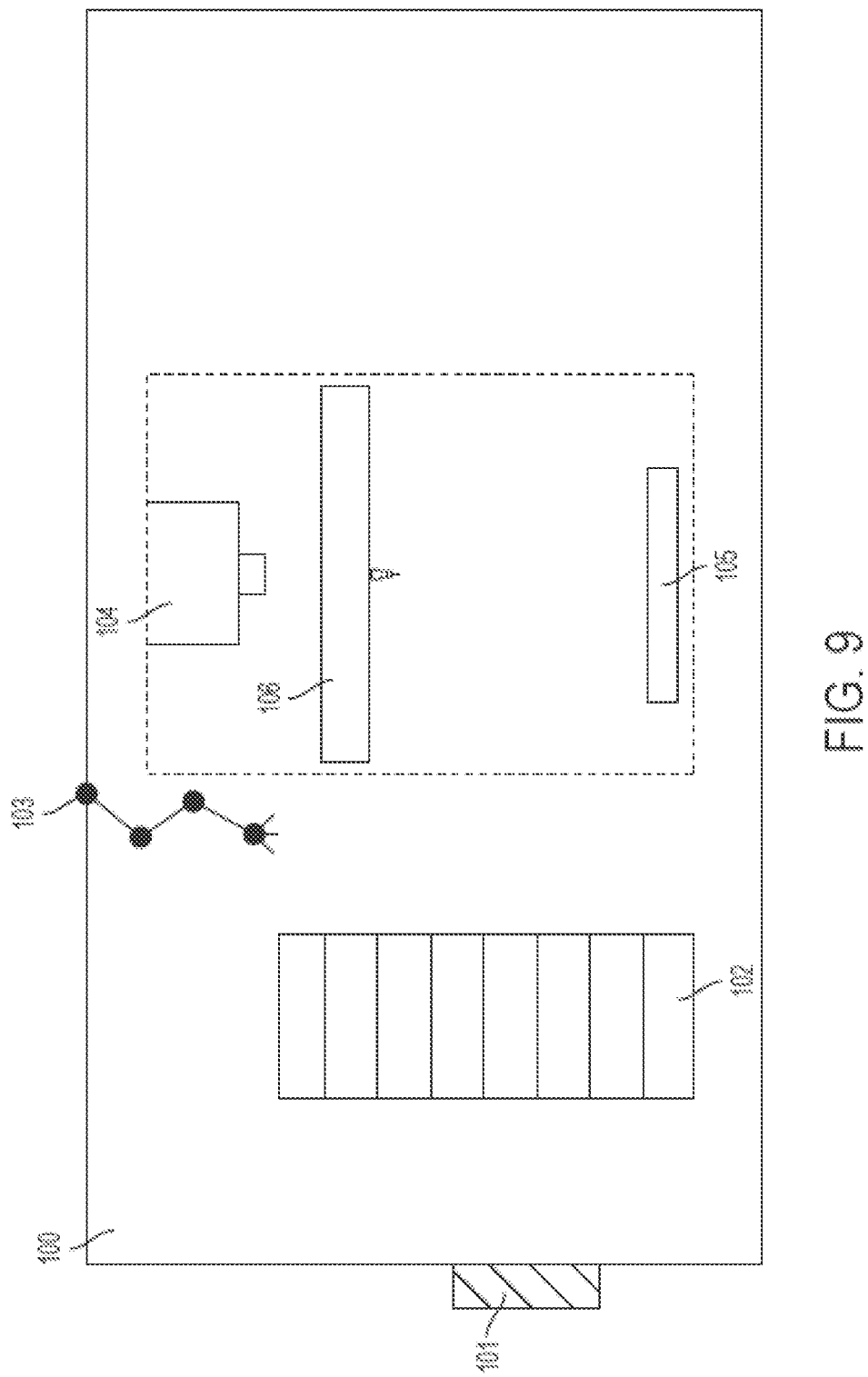

FIG. 9 depicts an illustrative embodiment of a cell culture incubator. In some embodiments, the cell culture incubator has an imaging location and a manipulation location that are the same location (105). As with prior embodiments, the manipulator (106) may be in fluid communication with one or more pipette tips (50) for transferring the volume of media containing cells into and out of the pipette tip(s).

Figure 10:
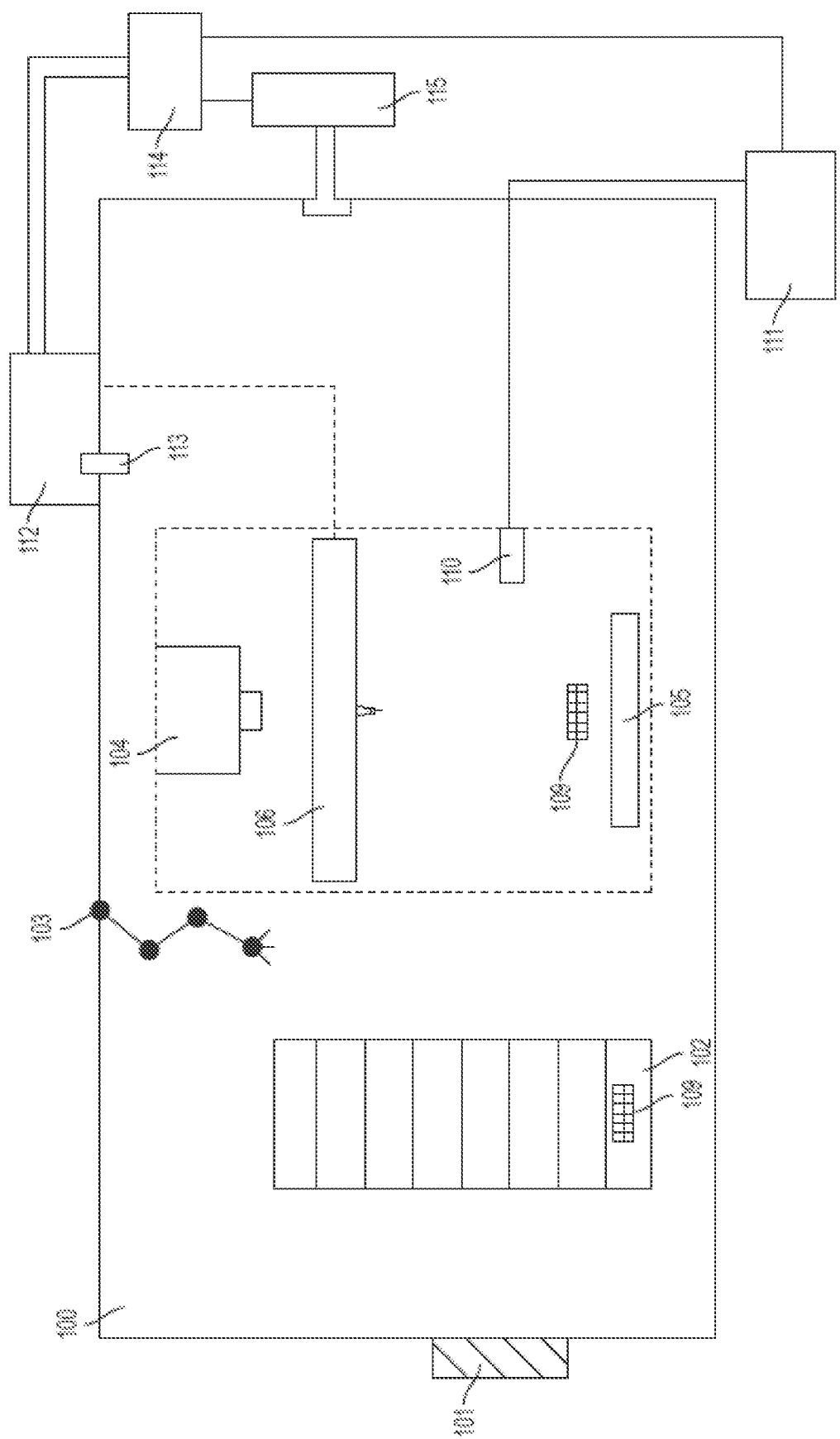
FIG. 10 is a schematic depicting further components of cell culture incubators.

FIG. 10 depicts illustrative embodiments of further components of a cell culture incubator. As will be appreciated, further components are any component of the incubator that is not otherwise listed or show in one of the previous embodiments or figures. In some embodiments, a cell culture incubator contains barcoded cell culture vessels (109). Thus, in some embodiments, a cell culture incubator has a barcode scanner (110) located inside the internal chamber of the incubator cabinet. In some embodiments, the barcode reader communicates with a computer (111) to relay information about the cell culture vessel for which the barcode has been scanned. In some cases, a barcode scanner may be affixed to any surface of the internal chamber. For example, a barcode scanner can be affixed to a wall of the internal chamber in close proximity to an imaging location (105).

In some embodiments, the cell culture incubator contains at least one probe and/or at least one sensor (113) that measures environmental conditions within the internal chamber.

Examples of probes to measure environmental conditions include but are not limited to temperature probes, pressure probes, carbon dioxide ($CO_2$) sensors, oxygen ($O_2$) sensors and relative humidity sensors. In some embodiments, the at least one probe and/or at least one sensor located within an instrument housing (112). The at least one probe and/or at least one sensor is connected to a controller (114). In some embodiments, the controller (114) communicates with a computer (111). Additionally, the controller (114) may communicate with a fluid dispensing system (115). For example, if a $CO_2$ sensor indicates a low $CO_2$ level in the internal chamber, the controller (114) may direct the fluid dispensing system (116) to inject $CO_2$ gas into the internal chamber in order to increase the $CO_2$ level of the internal chamber.

As will be appreciated, the controller (114) also may communicate with the manipulator (106) to transfer a volume of liquid into and out of the pipette tip (50). For example, the controller may instruct the manipulator (106) to position the pipette tip into a cell culture vessel. Next, the controller may instruct the manipulator to apply a first pressure (e.g., a negative pressure) to the second end (54) of the pipette tip (50) (e.g., to the membrane (60) to draw a volume of media containing the cells of the cell culture into the body of the pipette and/or into the bladder (58). The controller (114) may thereafter instruct the manipulator (106) to apply a second pressure to the second end of the pipette tip (50) to expel the volume of media from the pipette tip (50). As will be appreciated, and as shown in FIGS. 5E and 5E, in response to the second pressure (e.g., air pressure), the bladder (58) may be moved back into the pipette tip (50) to dispense a volume of liquid from the pipette tip (50).

Figure 11B:
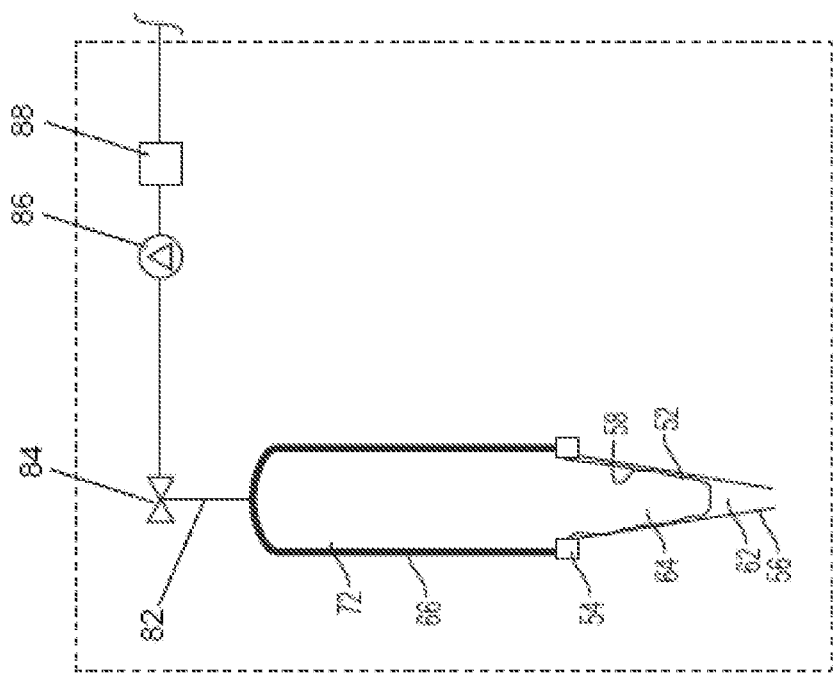
FIGS. 11A and 11B are schematic representations of a pipette arranged to apply a pressure to a pipette tip.
Figure 11A:
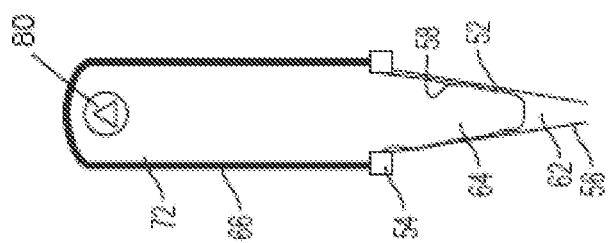

In some embodiments, the bladder is arranged to separate the liquid in the pipette tip (50) from a source of air and/or a vacuum source. As shown in FIG. 11A, the bladder may separate the liquid from a pump (80) in the body (72) of the pipette (66). As will be appreciated, the pump (80) is used to apply the pressure to the bladder (58). In other embodiments, as shown in FIG. 11B, the bladder (58) may separate the liquid from a liquid conduit (82) that applies the pressure to the bladder (58). In such embodiments, the liquid conduit (82) may be connected to a valve (84), a pump (86) and a supply (88) of pressurized air or fluid, which regulate and apply the pressure that is applied to the bladder (58). As will be appreciated, either the system may be used in the cell culture incubator.

As will be further appreciated, although embodiments are shown and described as having a bladder in the body, in other embodiments, the membrane may form other structures suitable for separating the liquid from the pipette and for allowing the pipette tip to be reused.

Figure 12:
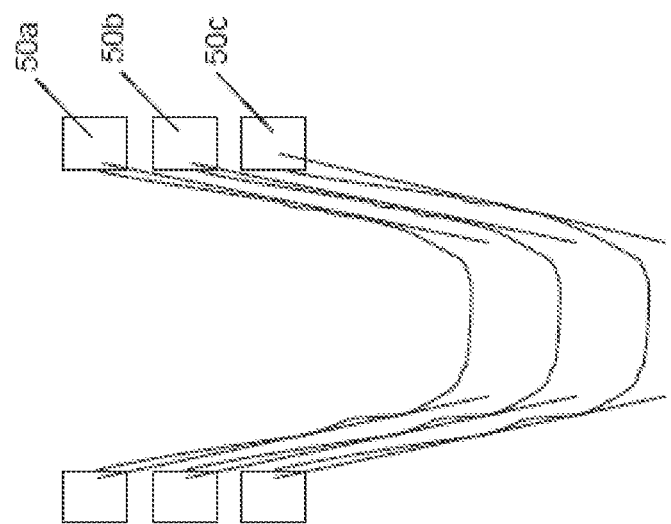
FIG. 12 is a schematic representation of nested pipette tips.
Figure 13:
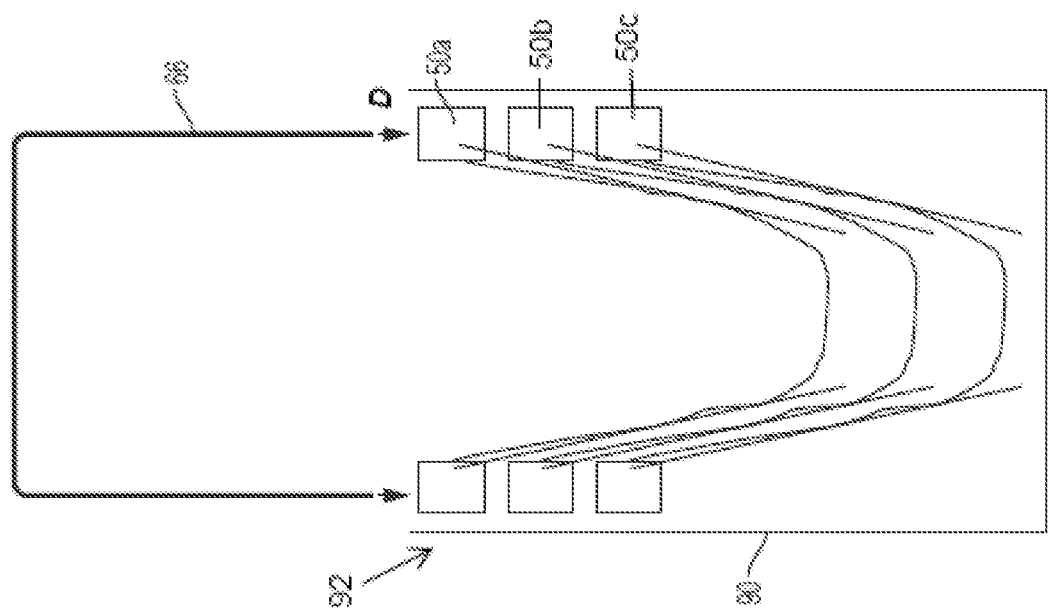
FIG. 13 is a schematic representation of a cartridge of pipette tips.

According to another aspect of the present document, as shown in FIGS. 12 and 13, the pipette tips (50) may be nestable. In that regard, a first pipette tip (50a) may be nested in a second pipette tip (50b), which, in turn, may be nested in a third pipette tip (50c). In some embodiments, the nested pipette tips may be compactly stored in a housing (90) of a cartridge (92), such as that shown in FIG. 13. In some embodiments, the cartridge (92) may be used to load the pipette tip (50) onto the pipette. As shown in FIG. 13, the pipette (66) may be moved towards the cartridge until the pipette is aligned with the pipette tip (50). The pipette may then be pressed downwardly towards the stack of pipette tips (see arrow labeled D) until the first or top pipette tip (50a) is attached to the pipette (66) (e.g., via a snap fit attachment). Such a loading process may be performed manually or may be automated.

As will be appreciated, although the cartridge shows three nested pipette tip (50), the cartridge may have more or fewer pipette tips in other embodiments. As will be further appreciated, while the pipette tips may be nested within the cartridge, the pipette tips may have other arrangements.

Automated Cell Culture

This document relates to incubators and methods for culturing, manipulating, and/or monitoring cells under controlled conditions (e.g., under aseptic and/or sterile conditions). In some aspects, incubators and methods include automated components. In some aspects, incubators and methods are useful for long term cell culture (e.g., to grow and maintain cells for recombinant protein expression or to grow and/or differentiate cells for therapeutic applications such as implantation). In some embodiments, cell cultures are grown within a culture vessel in an incubator described herein.

Culture Vessel

Cell culture vessels may be configured for culturing cells of different types, including eukaryotic or prokaryotic cells. In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis,* or *Pischia pastoris* cells, or bacterial cells such as *Escherichia coli, Bacillus subtilis,* or *Corynebacterium* cells), insect cells (e.g., *Drosophila* cells, or Sf9 or Sf21 cells), plant cells (e.g., algal cells) or cells of any other type.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example, HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells) and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, *Xenopus* cell lines, plant cell lines, or any other cell. In some embodiments, cells are human 293 cells (e.g., 293-T or HEK 293 cells), murine 3T3 cells, Chinese hamster ovary (CHO) cells, CML T1 cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to, solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators described herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

Primary Cell Isolation

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or pronase are used to digest the extracellular matrix. In some embodiments, tissue or biological samples are placed in culture medium (e.g., with or without physical or enzymatic disruption), and cells that are released and that grow in the culture medium can be isolated for further culture.

Cell Culture

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated within the incubators.

In some aspects, devices and methods described herein provide and maintain appropriate temperature and gas mixtures for cell growth. It should be appreciated that cell growth conditions differ for different cell types and that devices described herein can be programmed to maintain different conditions. In some embodiments, conditions of approximately 37° C., and 5% $CO_2$ are used for mammalian cells.

In some embodiments, devices and methods described herein are used to generate appropriate pressures for aspirating and/or dispensing liquid from the pipette tips. For example a manipulator (106) may include sensors that monitor the pressure being applied to the bladder (e.g., the pressure differential between the air pressure in the pipette tip and the air pressure of the environment). In some embodiments, devices and methods described herein are used to modify or change the culture media or conditions and/or to passage the cells when appropriate. In some embodiments, the devices and methods are automated (e.g., controlled by a controller (114) and/or computer (111), as shown in FIG. 7).

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture in incubators and vessels described herein. For example, cell cultures may be transfected with nucleic acids (e.g., DNA or RNA) or exposed to viral infection (e.g., using recombinant virus particles to deliver DNA or RNA).

Aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example in an environment (e.g., within an incubator chamber) that has been disinfected and in which the air has been filtered to remove potential contaminants.

In some embodiments, cell cultures are grown and maintained under GMP-compliant conditions, including using GMP-compliant media or GMP-compliant liquid handling equipment and performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by *mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells being grown in culture (e.g., mammalian cells). In some embodiments, one or more molecular detection assays (e.g., PCR, ELISA, RNA labeling, or other enzymatic techniques) or cell-based assays can be used to detect contamination (e.g., *mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat—STR—fingerprinting), isoenzyme analysis, human lymphocyte antigen (HLA) typing, chromosomal analysis, karyotyping, cell morphology, or other techniques.

In some embodiments, cells produced using devices and methods provided herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be present in or in proximity with an incubator to facilitate freezing of cells isolated from cell cultures.

Cell Culture Incubators:

This document relates to incubators and methods for culturing, manipulating, and/or monitoring cells under controlled conditions (e.g., under aseptic and/or sterile conditions). In some embodiments, the cell culture incubators provided herein include an incubator cabinet defining an internal chamber for incubation of cells in one or more cell culture vessels, in which the internal chamber is configured to hold the one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example to provide alternative access to the internal chamber during periods of time when the incubator is not operational, e.g., during maintenance of the incubator. In some embodiments, the incubators include a storage location within the internal chamber for storing one or more cell culture vessels. In some embodiments, a cell culture vessel transfer device is provided in the incubator for moving one or more cell culture vessels from a first imaging location to a storage location and/or from a storage location to an first imaging location.

In some embodiments, incubators or incubator cabinets provided herein are rectangularly cuboidal in shape. In some embodiments incubators or incubator cabinets provided herein have a rectangular footprint in a range of 1 ft$^2$ to 16 ft$^2$. In some embodiments incubators or incubator cabinets provided herein have a rectangular footprint of up to about 1 ft$^2$, 2 ft$^2$, 3 ft$^2$, 4 ft$^2$, 5 ft$^2$, 6 ft$^2$, 7 ft$^2$, 8 ft$^2$, 9 ft$^2$, 10 ft$^2$, 11 ft$^2$, 12 ft$^2$, 13 ft$^2$, 14 ft$^2$, 15 ft$^2$, or 16 ft$^2$. In some embodiments incubators or incubator cabinets provided herein have a total chamber volume in a range of 1 ft$^3$ to 100 ft$^3$. In some embodiments incubators or incubator cabinets provided herein have a chamber volume of up to about 1 ft$^3$, 5 ft$^3$, 10 ft$^3$, 25 ft$^3$, 50 ft$^3$ or 100 ft$^3$. In some embodiments incubators or incubator cabinets provided herein have a rectangular footprint in a range of 0.09 m$^2$ to 1.78 m$^2$. In some embodiments incubators or incubator cabinets provided herein have a rectangular footprint of up to about 0.1 m$^2$, 0.2 m$^2$, 0.3 m$^2$, 0.4 m$^2$, 0.5 m$^2$, 0.6 m$^2$, 0.7 m$^2$, 0.8 m$^2$, 0.9 m$^2$, 1.0 m$^2$, 1.1 m$^2$, 1.2 m, 1.3 m$^2$, 1.4 m$^2$, 1.5 m$^2$, 1.6 m$^2$, or 1.7 m$^2$. In some embodiments, incubators or incubator cabinets provided herein have a total chamber volume in a range of 0.03 m$^3$ to 3 m$^3$. In some embodiments incubators or incubator cabinets provided herein have a chamber volume of up to about 0.03 m$^3$, 0.1 m$^3$, 0.3 m$^3$, 1 m$^3$, or 3 m$^3$.

Materials

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

Monitoring Equipment

In some embodiments, the environment inside an incubator is controlled by a control system that may be configured to control the temperature, humidity, carbon dioxide, oxygen, and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator is further provided with a monitoring system with predefined sensors. Examples of monitoring devices include, but are not limited, to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, $N_2$, $CO_2$, $O_2$, and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents.

In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator). In some embodiments, one or more controllers are attached to the sensors and other systems to control the internal environment of the incubator.

In some embodiments, an incubator can include one or more light sources (e.g., an incandescent bulb, LED, UV or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

Seals

In some embodiments, a culture cabinet includes windows, doors, or openings that when closed are sealed to preserve sterility after the incubator cabinet has been sterilized. In some embodiments, each seal of the incubator cabinet is air tight up to a threshold level of pressure (e.g., up to 1 atm). In some embodiments, a gasket is provide to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoro-ethylene). It is often desirable that a gasket be made from a material that provides some degree of yielding such that it is able to deform and tightly fills the space it is designed for, including any slight irregularities. In some embodiments, gaskets can be used with an application of sealant directly to the gasket surface to function properly. In some embodiments, a gasket material can include a closed-cell neoprene foam which is non-reactant with carbon dioxide or ozone.

Transfer Devices

Incubators disclosed herein typically include one or more transfer devices for moving one or more items, e.g., from a first location to a second location, within the incubators. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In some embodiments, a transfer device includes a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further includes a gripper assembly coupled to a robotic arm. In some embodiments, the gripper assembly includes one or more grippers mounted on the end of the robotic arm, each gripper having two or more (e.g., 3, 4, 5, or more) gripper fingers. In some embodiments, each of the gripper fingers on the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, or the platform, or a separate absolute encoder for each of the gripper assembly and/or the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt, located, for example, on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components from a transport line of the laboratory automation system into the incubator cabinet or transport external assay components into and/or out of the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are is located. In some cases, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to position properly the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner.

In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate, or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel, and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself can be configured to determine the height or other dimensions of the vessel or other container. Using this information, the robotic arm may be requested to transport a particular container, such as when an analytical module is ready to perform an assay or other manipulation on cells grown in the vessels or has completed performing an assay or manipulation.

Computer and Control Equipment

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, a manipulator attached to the disclosed pipette tip, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Cell Assays

In some embodiments, incubator cabinets provided herein are configured with a microscope or other imager or other device for purposes of monitoring cell growth, viability or other aspect of cells. In some embodiments, the microscope or imager is used in conjunction with an assay performed within the incubator cabinet, such as an image based phenotypic screen or assay.

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

Treatments and Experimental Interventions

In certain embodiments, incubators provided herein are configured to permit high-throughput screening (HTS) within an incubator cabinet. In some embodiments, HTS refers to testing of up to, for example, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays described herein involve the use of automation. In some embodiments, an integrated robot system that includes of one or more robotic arms transports assay microplates between multiple assay stations for compound, cell, and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

The above aspects and embodiments may be employed in any suitable combination, as the present invention is not limited in this respect.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A pipette tip comprising:
    a pipette tip body defining an inner volume and having first and second ends, the first end arranged to pass a liquid into and out of the pipette tip and the second end arranged for attachment to a pipette having a pipette body;
    a bladder sealingly attached to the pipette tip body, wherein the bladder includes a membranous sac in a collapsed configuration disposed in the inner volume; and
    a pipette shell within the pipette body and receptive of the bladder in response to an applied pressure.

2. The pipette tip of claim 1, wherein the bladder is disposable in the inner volume of the pipette tip body.

3. The pipette tip of claim 1, wherein the bladder is arranged to cause a volume of liquid to be drawn into or expelled from the inner volume though the first end in response to a pressure gradient applied across the bladder.

4. The pipette tip of claim 1, wherein the bladder is arranged to permit a volume of liquid to be drawn into the inner volume of the pipette tip body through the first end in response to a negative pressure gradient directed from the first end toward the second end and across the bladder, and wherein the bladder is arranged to permit a volume of liquid to be expelled from the inner volume of the pipette tip body through the first end in response to a positive pressure gradient directed from the first end toward the second end and across the bladder.

5. The pipette tip of claim 4, wherein the bladder has a first side and a second side, wherein the first side faces the first end of the pipette tip body, and wherein the negative pressure gradient is generated by drawing a vacuum on the second side.

6. The pipette tip of claim 1, wherein the bladder is attached to the pipette tip body at one of the first and second ends of the pipette tip body.

7. The pipette tip of claim 1, wherein the bladder is attached to the pipette tip body at a location between the first and second ends of the pipette tip body.

8. The pipette tip of claim 1, wherein the pipette shell is removably attachable to the pipette tip.

9. The pipette tip of claim 1, wherein the bladder is expandable to be at least partially disposed outside of the inner volume.

10. The pipette tip of claim 1, wherein the pipette shell has a volume at least equal to a volume of the bladder.

11. The pipette tip of claim 1, wherein the bladder provides a seal between a first compartment defined between a first side of the bladder and the first end of the pipette tip body and a second compartment defined between a second side of the bladder and the pipette.

12. The pipette tip of claim 11, wherein the bladder provides a seal while liquid is drawn into the first compartment.

13. The pipette tip of claim 1, wherein the sac is permanently attached to the pipette tip body at a periphery thereof.

14. A combination of the pipette tip of claim 1, in combination with a second pipette tip, the second pipette tip comprising:
    a second body defining a second inner volume and having third and fourth ends, the third end arranged to pass a liquid into and out of the second pipette tip and the fourth end arranged for attachment to a pipette; and
    a second bladder sealingly attached to the second body;
    wherein the first and second pipette tips are nestable.

15. The combination of claim 14, wherein the second bladder is disposable in the second inner volume.

16. The combination of claim 14, wherein the first pipette tip is nested on top of the second pipette tip.

17. The combination of claim 16, wherein the second bladder is adjacent to the body of the first pipette tip when the first pipette tip is nested on top of the second pipette tip.

18. The pipette tip of claim 1, wherein, in response to a first applied pressure, the bladder is arranged to move in a direction away from the first end of the pipette tip body to draw a volume of liquid into the pipette tip.

19. The pipette tip of claim 18, wherein, in response to a second applied pressure, the bladder is arranged to move in a direction toward the first end of the pipette tip body to transfer a volume of liquid out of the pipette tip.

20. The pipette tip of claim 18, wherein, in response to the first applied pressure, at least a portion of the bladder is arranged to accommodate a volume of liquid.

21. The pipette tip of claim 18, wherein the volume of liquid drawn into the pipette tip is proportional to an amplitude of the first applied pressure.

22. A pipette tip comprising:
    a pipette tip body defining an inner volume and having first and second ends, the first end arranged to pass a liquid into and out of the pipette tip and the second end arranged for attachment to a pipette having a pipette body;
    a bladder sealingly attached to the pipette tip body, wherein the bladder includes a membranous sac in a collapsed configuration disposed in the inner volume and wherein the bladder and at least a portion of the inner volume are arranged to accommodate a volume of liquid; and
    a pipette shell within the pipette body and receptive of the bladder in response to an applied pressure.

* * * * *